(12) United States Patent
Yu et al.

(10) Patent No.: US 11,016,013 B2
(45) Date of Patent: May 25, 2021

(54) APPARATUS FOR MEASURING BLOOD COAGULATION DATA, AND USE METHOD AND CALIBRATION METHOD THEREOF

(71) Applicant: NEOTEK BIOSCIENCE CO., LTD., Jiangsu (CN)

(72) Inventors: Bangzhong Yu, Jiangsu (CN); Feng Jiang, Jiangsu (CN)

(73) Assignee: NEOTEK BIOSCIENCE CO., LTD., Jiangsu (CN)

( * ) Notice: Subject to any disclaimer, the term of this patent is extended or adjusted under 35 U.S.C. 154(b) by 189 days.

(21) Appl. No.: 16/097,565

(22) PCT Filed: May 2, 2017

(86) PCT No.: PCT/CN2017/082754
§ 371 (c)(1),
(2) Date: Oct. 29, 2018

(87) PCT Pub. No.: WO2017/186183
PCT Pub. Date: Nov. 2, 2017

(65) Prior Publication Data
US 2019/0162641 A1 May 30, 2019

(30) Foreign Application Priority Data

Apr. 29, 2016 (CN) .......................... 201610278391.2
Apr. 29, 2016 (CN) .......................... 201620380641.9
(Continued)

(51) Int. Cl.
*G01N 11/16* (2006.01)
*G01N 11/14* (2006.01)
(Continued)

(52) U.S. Cl.
CPC ......... *G01N 11/162* (2013.01); *G01N 11/142* (2013.01); *G01N 33/4905* (2013.01); *G01N 27/74* (2013.01); *G01N 2011/147* (2013.01)

(58) Field of Classification Search
CPC .......................... G01N 11/162; G01N 11/142
(Continued)

(56) References Cited

U.S. PATENT DOCUMENTS 4,193,293 A 3/1980 Cavallari
7,775,664 B2 8/2010 Saito et al.

FOREIGN PATENT DOCUMENTS

CN 101322643 A 12/2008
CN 201666795 U * 12/2010
(Continued)

OTHER PUBLICATIONS

International Search Report issued for International Patent Application No. PCT/CN2017/082754, dated Aug. 2, 2017, 11 pages including English translation.

*Primary Examiner* — Tarun Sinha
(74) *Attorney, Agent, or Firm* — Hamre. Schumann, Mueller & Larson, P.C.

(57) ABSTRACT

An apparatus for measuring blood coagulation data, and a use method and calibration method thereof are disclosed. The apparatus comprises: a movable support part (101), a fixed support part (102), a connection part (103), a rotary shaft (104), a magnet (105), a Hall element (106), and a processing unit (107). One end of the movable support part (101) is fixedly connected to the rotary shaft (104), and the other end of the movable support part (101) is connected to the fixed support part (102) by means of the connection part (103); the movable support part (101) is fixedly connected to the magnet (105); the rotary shaft (104) is able to rotate relative to the fixed support part (102) under the driving force of measured blood and drive the movable support part (Continued)

(101) to rotate; the movable support part (101) is able to move the magnet (105) to cause a change in the magnetic field of the magnet (105); the Hall element (106) is connected to the processing unit (107); the Hall element (106) is used for outputting a measurement electric signal according to the magnetic field change of the magnet (105); and the processing unit (107) is used for determining blood coagulation data of the measured blood according to the measurement electric signal. The present apparatus can improve the accuracy in measurement of blood coagulation data.

15 Claims, 13 Drawing Sheets

(30) Foreign Application Priority Data

Aug. 30, 2016 (CN) .......................... 201610754356.3
Aug. 30, 2016 (CN) .......................... 201610754599.7
Aug. 30, 2016 (CN) .......................... 201610755517.0

(51) Int. Cl.
*G01N 33/49* (2006.01)
*G01N 27/74* (2006.01)

(58) Field of Classification Search
USPC ........................................................ 73/54.33
See application file for complete search history.

(56) References Cited

FOREIGN PATENT DOCUMENTS

| CN | 201666795 U | | 12/2010 |
|---|---|---|---|
| CN | 102830041 A | | 12/2012 |
| CN | 104181311 A | * | 12/2014 |
| CN | 104181311 A | | 12/2014 |
| CN | 104614539 A | | 5/2015 |
| CN | 105805176 A | | 7/2016 |
| CN | 105807039 A | | 7/2016 |
| CN | 205744966 U | | 11/2016 |
| CN | 106404888 A | | 2/2017 |
| CN | 106442702 A | | 2/2017 |
| CN | 106442952 A | | 2/2017 |

* cited by examiner

APPARATUS FOR MEASURING BLOOD COAGULATION DATA, AND USE METHOD AND CALIBRATION METHOD THEREOF

TECHNICAL FIELD

The present invention relates to the technical field of measurement, and in particular, to an apparatus for measuring blood coagulation data, and a use method and calibration method thereof.

BACKGROUND

An apparatus for measuring blood coagulation data, such as a thrombelastography device, is an apparatus which is configured to measure blood coagulation data of blood in vitro, and monitor the blood coagulation process from entire dynamic processes, such as platelet aggregation, blood coagulation and fibrinolysis, thereby obtaining rates of blood coagulation and fibrinolysis, the strength of coagulation and the like. The rates of blood coagulation and fibrinolysis and the strength of coagulation can be used as a basis for clinical diagnosis of diseases, such as cardiovascular and cerebrovascular diseases.

SUMMARY

An embodiment of the present invention provides an apparatus for measuring blood coagulation data, and a use method and calibration method thereof, which can improve the measurement accuracy of the blood coagulation data.

An apparatus for measuring blood coagulation data provided by an embodiment of the present invention comprises a movable support part, a fixed support part, a connection part, a rotary shaft, a magnet, a Hall element and a processing unit, wherein one end of the movable support part is fixedly connected to the rotary shaft, and the other end of the movable support part is connected to the fixed support part by means of the connection part;

the movable support part is fixedly connected to the magnet;

the rotary shaft is able to rotate relative to the fixed support part under the driving force of measured blood and drive the movable support part to rotate;

the movable support part is able to move the magnet to cause a change in the magnetic field of the magnet;

the Hall element is connected to the processing unit;

the Hall element is used for outputting a measurement electric signal according to the magnetic field change of the magnet; and the processing unit is used for determining blood coagulation data of the measured blood according to the measurement electric signal.

In the embodiment of the present invention, the rotary shaft is able to rotate relative to the fixed support part under the driving force of measured blood and drive the movable support part to rotate; the movable support part is able to move the magnet to cause a change in the magnetic field of the magnet; the Hall element is used for outputting a measurement electric signal according to the magnetic field change of the magnet; and the processing unit is used for determining blood coagulation data of the measured blood according to the measurement electric signal. The Hall element has good stability and high precision and improves the measurement accuracy of the blood coagulation data.

BRIEF DESCRIPTION OF THE DRAWINGS

In order to illustrate the embodiments of the present invention or the technical solutions in the prior art more clearly, the drawings used in the embodiments or the prior art description will be briefly described below. Apparently, the drawings in the following description are some embodiments of the present invention. For those of ordinary skill in the art, other drawings may also be obtained according to these drawings, without paying creative work.

DETAILED DESCRIPTION

In order to make the objective, the technical solution and the advantages of the embodiments of the present invention clearer, the technical solutions in the embodiments of the present invention are clearly and completely described below with reference to the accompanying drawings in the embodiments of the present invention. It is apparent that the described embodiments are part of the embodiments of the present invention, rather than all of the embodiments. All other embodiments obtained by those of ordinary skill in the art based on the embodiments of the present invention without paying creative work should fall within the protection scope of the present invention.

Figure 1:
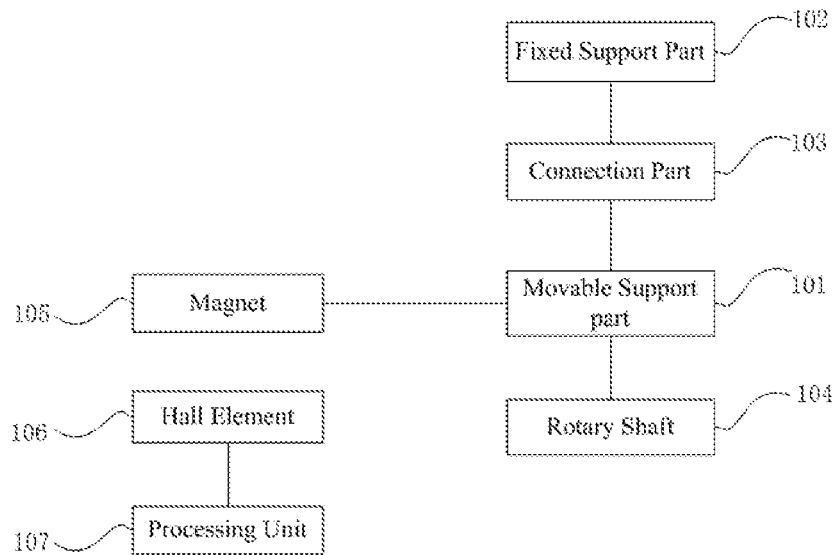
FIG. 1 is a schematic diagram of an apparatus for measuring blood coagulation data as provided by an embodiment of the present invention.

As shown in FIG. 1, an embodiment of the present invention provides an apparatus for measuring blood coagulation data. The apparatus comprises a movable support part 101, a fixed support part 102, a connection part 103, a rotary shaft 104, a magnet 105, a Hall element 106 and a processing unit 107;

one end of the movable support part 101 is fixedly connected to the rotary shaft 104, and the other end of the movable support part 101 is connected to the fixed support part 102 by means of the connection part 103;

the movable support part 101 is fixedly connected to the magnet 105;

the rotary shaft 104 is able to rotate relative to the fixed support part 102 under the driving force of measured blood and drive the movable support part 101 to rotate;

the movable support part 101 is able to move the magnet 105 to cause a change in the magnetic field of the magnet 105;

the Hall element 106 is connected to the processing unit 107;

the Hall element 106 is used for outputting a measurement electric signal according to the magnetic field change of the magnet 105; and the processing unit 107 is used for determining blood coagulation data of the measured blood according to the measurement electric signal.

In the embodiment of the present invention, the rotary shaft is able to rotate relative to the fixed support part under the driving force of measured blood and drive the movable support part to rotate; the movable support part is able to move the magnet to cause a change in the magnetic field of the magnet; the Hall element is used for outputting a measurement electric signal according to the magnetic field change of the magnet; and the processing unit is used for determining blood coagulation data of the measured blood according to the measurement electric signal. The Hall element has good stability and high precision and improves the measurement accuracy of the blood coagulation data.

In the embodiment of the present invention, when the magnet moves with the movable support part, the direction of the magnetic field of the magnet will change. Since the Hall element is located in the magnetic field generated by the magnet, the magnetic field generated by the magnet will change with respect to the Hall element. For example, as the direction of the magnetic field of the magnet changes, the number of magnetic lines passing through a sensing surface of the Hall element in the magnetic field changes. As the magnetic field of the magnet changes, the Hall element outputs a corresponding measurement electric signal.

In an embodiment of the present invention, the Hall element is fixedly connected to the fixed support part. When the rotary shaft rotates relative to the fixed support part under the driving force of measured blood, the magnet rotates relative to the fixed support part along with the movable support part. Since the Hall element is fixedly connected to the fixed support part, the magnet rotates relative to the Hall element along with the movable support part, and further the magnetic field around the Hall element changes in direction relative to the Hall element. The magnetic lines that can be measured by the Hall element changes, and then, the Hall element outputs the corresponding measurement electric signal.

In an embodiment of the present invention, the Hall element comprises a Hall sheet, wherein an N pole and an S pole of the magnet are located on the same plane. An included angle between a plane where the Hall sheet is located and the plane where the N pole and the S pole of the magnet are located is (0°, 90°].

When the N pole and the S pole of the magnet are located on the same plane, the magnetic lines between the N pole and the S pole are distributed more uniformly. When the magnet rotates with the rotation of the rotary shaft, in a position where the Hall sheet is located, the magnetic field generated by the magnet changes uniformly, such that the Hall sheet can sense the magnetic field change of the magnet accurately, thereby contributing to improving the measurement accuracy of the blood coagulation data.

Since the Hall sheet is in a flaky shape, the number of magnetic lines passing through the Hall sheet is mainly determined by the number of magnetic lines passing through the two surfaces having the largest areas of the Hall sheet. When the included angle between the plane where the Hall sheet is located and the plane where the N pole and the S pole of the magnet coexist is (0°, 90°], as the magnet rotates, the number of magnetic lines passing through the sensing surface of the Hall element changes along with the rotation angle of the rotary shaft. That is, the magnetic induction intensity of the magnetic field measured by the Hall element changes along with the rotation angle, and the measurement electric signal outputted by the Hall element also changes with the rotation angle. For example, assuming that the Hall element is in a uniform magnetic field, when the sensing surface of the Hall element is perpendicular to the direction of the magnetic field, the number of the magnetic lines passing through the Hall sheet is maximum, the magnetic induction intensity measured by the Hall element is maximum, and the output voltage is also highest; when the sensing surface of the Hall element is parallel to the direction of the magnetic field, the number of the magnetic lines passing through the Hall sheet is minimum, the magnetic induction intensity measured by the Hall element is minimum, and the output voltage is also lowest.

Of course, the Hall element may also be of other shapes. Regardless of the shape of the Hall element, a positional relationship between the Hall element and the magnet can only satisfy the following condition: when the magnet moves with the movable support part, the magnetic induction intensity measured by the Hall element has a certain relationship with the rotation angle of the movable support part.

Figure 2:
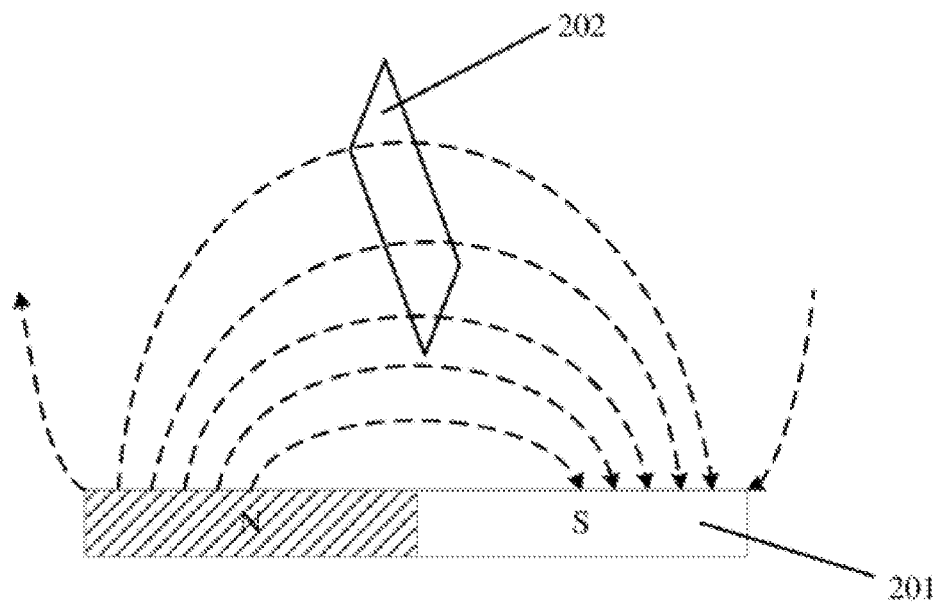
FIG. 2 is a schematic diagram of a positional relationship between a Hall sheet and a magnet as provided by an embodiment of the present invention.

FIG. 2 is a schematic diagram of a positional relationship between the magnet and the Hall sheet. The dotted lines in FIG. 2 are the magnetic lines generated by the magnet. As can be seen from FIG. 2, as the magnet 201 rotates, the number of magnetic lines passing through the Hall sheet 202 changes.

Figure 3:
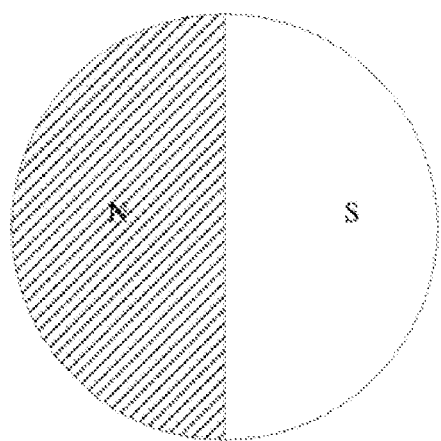
FIG. 3 is a schematic diagram of a magnet provided by an embodiment of the present invention.
Figure 4:
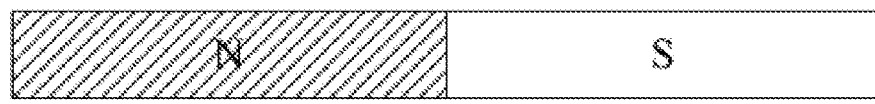
FIG. 4 is a schematic diagram of a magnet provided by another embodiment of the present invention.

As shown in FIG. 3, the magnet may be in a shape of a disk, wherein the N pole of the magnet is semicircular, and the S pole of the magnet is semicircular. As shown in FIG. 4, the magnet may be in a shape of a strip, wherein the N pole of the magnet is a half of the strip, and the S pole of the magnet is a half of the strip.

Figure 5:
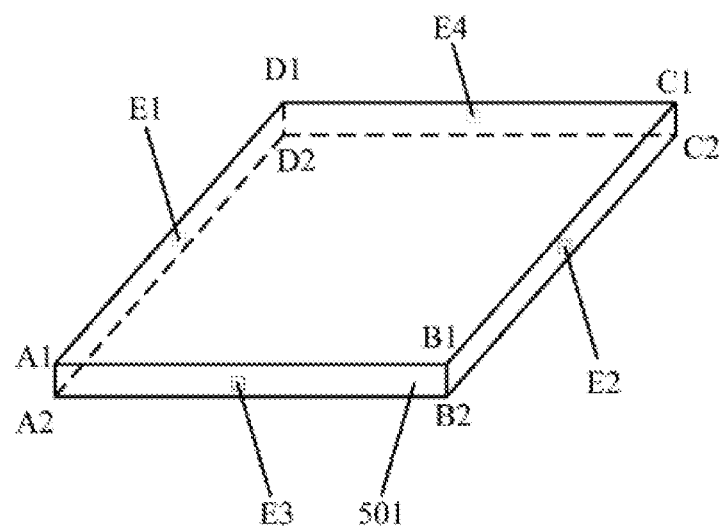
FIG. 5 is a schematic diagram of a Hall element as provided by an embodiment of the present invention.

As shown in FIG. 5, a Hall element provided by an embodiment of the present invention comprises a Hall sheet 501 which may be a semiconductor sheet. The Hall sheet 501 has four electrodes, which are E1, E2, E3, and E4, respectively. E1 and E2 are current electrodes which are powered by an operating current I, and E3, and E4 are voltage electrodes which output a Hall voltage VH. The thickness of the Hall sheet is d, and the Hall coefficient is RH. The Hall sheet may be made of Ge, Si, InSb, GaAs, InAs, InAsP, and a multilayer semiconductor heterostructure quantum well material. The thickness of the Hall sheet may be 0.05 mm or less, for example, the thickness is 0.02 mm or 0.01 mm. The Hall element may be realized by the following chips: SS541AT, SS543GT, SS513AT, SS513GT, VF526DT, HG-302C, HG-302A, HG-362A, HW-300B, HW-302B, HW-322B, or the like. As shown in FIG. 5, eight vertices of the Hall sheet are A1, B1, C1, D1, A2, B2, C2, and D2.

Figure 6:
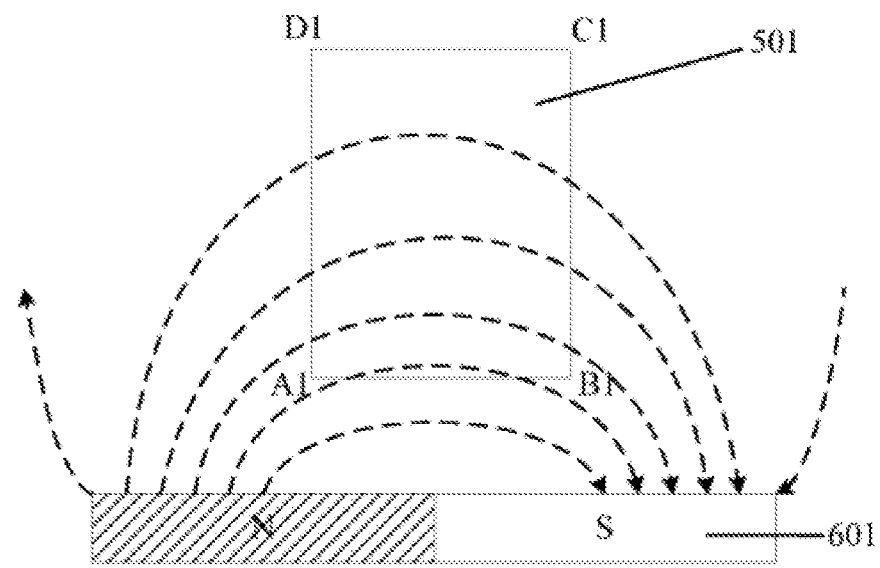
FIG. 6 is a schematic diagram of a positional relationship between a Hall sheet and a magnet as provided by another embodiment of the present invention.
Figure 7:
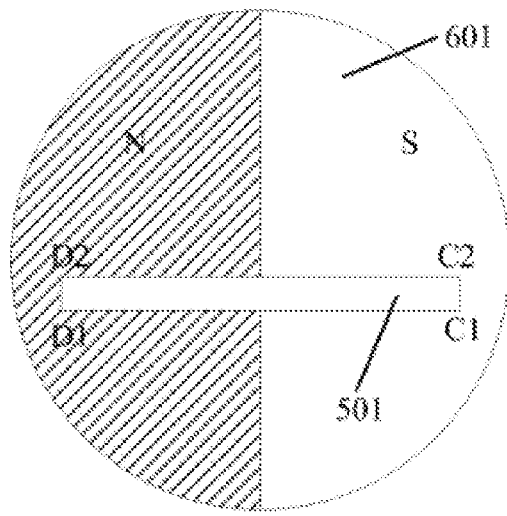
FIG. 7 is a schematic diagram of a positional relationship between a Hall sheet and a magnet as provided by a further embodiment of the present invention.

The Hall element as shown in FIG. 5 is fixedly connected to the fixed support part. When the rotary shaft is not driven by an external force and no rotation occurs, the positional relationship between the Hall sheet 501 of the Hall element and the magnet 601 is as shown in FIG. 6. FIG. 6 shows a vertical section of the magnet 601. The magnet in FIG. 6 may be the magnet shown in FIG. 3. In the case where the magnet is the magnet shown in FIG. 3, when the rotary shaft is not driven by an external force and no rotation occurs, the positional relationship between the Hall sheet 501 and the magnet 601 shown in FIG. 5 is as shown in FIG. 7. FIG. 7 is a top view. Specifically, as can be seen from FIG. 7, the plane where the Hall sheet 501 is located is perpendicular to the upper surface of the magnet 601.

Based on the Hall sheet and the magnet 601 shown in FIG. 7, the rotation angle of the rotary shaft satisfies a formula I:

$$\sin\theta = \frac{V_H \times d}{R_H \times I \times B}$$

in which, θ is the rotation angle of the rotary shaft, VH is the Hall voltage outputted by the Hall element, d is the thickness of the Hall sheet in the Hall element, I is the operating current I of the Hall element 501, and B is the magnetic induction intensity of the magnetic field where the Hall sheet 501 is located.

For example, the operating current of the Hall element may be 3 mA, the thickness of the Hall sheet in the Hall element is 0.01 mm, and the Hall coefficient of the Hall element is 0.00692 cubic meters per coulomb.

Based on the Hall sheet 501 and the magnet 601 shown in FIG. 7, the processing unit is specifically configured to determine the rotation angle of the rotary shaft according to Formula 1, and determine blood coagulation data of measured blood according to the rotation angle.

In the embodiment of the present invention, in order to make the blood coagulation data of the measured blood more accurate, it is necessary to reduce the frictional force between the movable support part which is in rotation and the fixed support part. In order to reduce the frictional force between the movable support part and the fixed support part, the connection part in the embodiment of the present invention may be implemented in the following manner:
in an embodiment of the present invention, the connection part comprises a rolling bearing, wherein
an inner ring of the rolling bearing is fixedly connected to the movable support part; and
an outer ring of the rolling bearing is fixedly connected to the fixed support part.

In the embodiment of the present invention, a rolling body which may be a ball, or the like is provided between the inner ring and the outer ring of the rolling bearing. The outer ring is fixedly connected to the fixed support part and remains stationary. The inner ring is fixedly connected to the movable support part and rotates with the movable support part. The rotary shaft rotates relative to the fixed support part under the driving force of the measured blood and drives the movable support part to rotate. The frictional force between the movable support part and the fixed support part is reduced by the rolling bearing, and the influence of the frictional force on the rotation of the movable support part is reduced, thereby reducing the influence of the frictional force on the magnetic field change of the magnet, so that the magnetic field change of the magnet reflects the blood coagulation data of the measured blood more accurately.

In an embodiment of the present invention, the connection part comprises a top cone and a jewel bearing, wherein
the jewel bearing is fixed on the fixed support part;
the top cone is fixed on the movable support part; and
a cone top of the top cone is connected to the jewel bearing in a form of point contact having a contact area smaller than a preset area.

In the embodiment of the present invention, the jewel bearing may be of a cake structure. A plane of the cake structure is provided with a tapered groove. The top cone may be of a tapered structure, and the cone top of the top cone is located in the tapered groove on the jewel bearing. Not all, but the cone top, of the top cone is in contact with the jewel bearing. The contact area between the cone top of the top cone and the jewel bearing is less than or equal to the preset area, wherein the preset area ranges from (0, 1] square millimeters, for example: the preset area is 1 square millimeter, and the area of the cone top of the top cone is 0.8 square millimeters, which meets the requirement.

In the embodiment of the present invention, the rotary shaft rotates relative to the fixed support part under the driving force of the measured blood and drives the movable support part to rotate. The movable support part rotates with the connection part as an axis. In the connection part, since the contact area between the top cone and the jewel bearing is relatively small, the frictional force between the top cone and the jewel bearing is relatively small. When the movable support part rotates with the rotary shaft, the frictional force has less resistance to the rotation, thereby reducing the influence of the frictional force on the magnetic field change of the magnet, so that the magnetic field change of the magnet reflects the blood coagulation data of the measured blood more accurately.

In order to further reduce the frictional force between the top cone and the jewel bearing, a third magnet and a fourth magnet are further included, wherein
the third magnet is fixed on the fixed support part;

the fourth magnet is fixed on the movable support part; and the third magnet and the fourth magnet are mutually exclusive, such that the frictional force between the top cone and the jewel bearing is reduced.

In the embodiment of the present invention, the pressure between the top cone and the jewel bearing may be reduced by the interactive force between the third magnet and the fourth magnet, thereby reducing the frictional force between the top cone and the jewel bearing. Therefore, the frictional force has less resistance to the rotation of the movable support part. For example, the third magnet and the fourth magnet are parallel to each other and parallel to a plane where the jewel bearing is located. In a vertical direction, the movable support part is supported by the acting force of the top cone and the jewel bearing in the vertical direction, and the acting force between the third magnet and the fourth magnet. In this way, the acting force of the top cone and the jewel bearing in the vertical direction is reduced, thereby reducing the frictional force between the top cone and the jewel bearing.

Figure 8A:
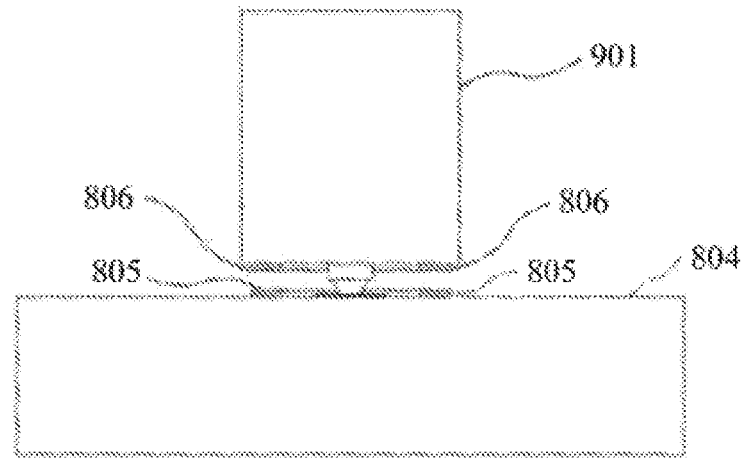
FIG. 8A is a schematic diagram of a positional relationship between a first magnet and a second magnet as provided by an embodiment of the present invention.

In an embodiment of the present invention, as shown in FIG. 8A, the connection part comprises a first magnet 805 and a second magnet 806, wherein the first magnet 805 is fixed on the fixed support part 804;

the second magnet 806 is fixed on the movable support part 901; and the magnetic force generated between the first magnet 805 and the second magnet 806 suspends the movable support part, so that there is no mechanical contact between the fixed support part 804 and the movable support part 901.

The connection part has a main function of connecting the movable support part and the fixed support part, such that the movable support part is able to rotate under the support of the fixed support part. In the embodiment of the present invention, the movable support part is supported by the interactive force between the first magnet and the second magnet. The movable support part suspends by using the magnetic force generated between the first magnet and the second magnet. There is no contact between the first magnet and the second magnet, and therefore no frictional force exists. The rotary shaft rotates relative to the fixed support part under the driving force of the measured blood and drives the movable support part to rotate. The movable support part rotates under a magnetic force generated between the first magnet and the second magnet of the connection part. In the connection part, there is no frictional force between the first magnet and the second magnet, thereby producing less resistance to the rotation of the movable support part, such that the magnetic field change of the magnet reflects the blood coagulation data of the measured blood more accurately.

For example, the first magnet and the second magnet are parallel to each other, the magnetic force between the first magnet and the second magnet can support the movable support part in the vertical direction, and there is no contact between the first magnet and the second magnet.

In an embodiment of the present invention, the apparatus further comprises at least one hair spring, wherein an inner ring of the hair spring is fixedly connected to an outer circumferential surface of the rotary shaft;

an outer ring of the hair spring is fixedly connected to the fixed support part; and the hair spring is configured to, after the rotary shaft rotates away from a balanced position of the rotary shaft, generate an acting force for rotating the rotary shaft towards the balanced position.

The balanced position of the rotary shaft is a position where the rotary shaft is located when the rotary shaft is not driven by the measured blood.

In the embodiment of the present invention, the inner ring of the hair spring is fixed to the rotary shaft, and the outer ring of the hair spring is connected to the fixed support part. When the rotary shaft rotates away from the balanced position under the driving force of the measured blood, the hair spring is screwed or unscrewed and then deforms to restore the elastic force. When the driving force of the measured blood is removed, the rotary shaft returns to the balanced position under the recovery elastic force, such that the rotary shaft is calibrated automatically, without an manual operation. Therefore, the efficiency of measuring the measured blood is further improved when different measured bloods are tested continuously.

In an embodiment of the present invention, when the apparatus for measuring the blood coagulation data comprises at least two hair springs, the spiral directions of at least two of the hair springs are opposite. In this way, when the rotary shaft rotates, the screwed hair spring and the unscrewed hair spring coexist, which prolongs the service life of the hair springs and ensures that the rotary shaft rotates more stably.

Figure 8B:
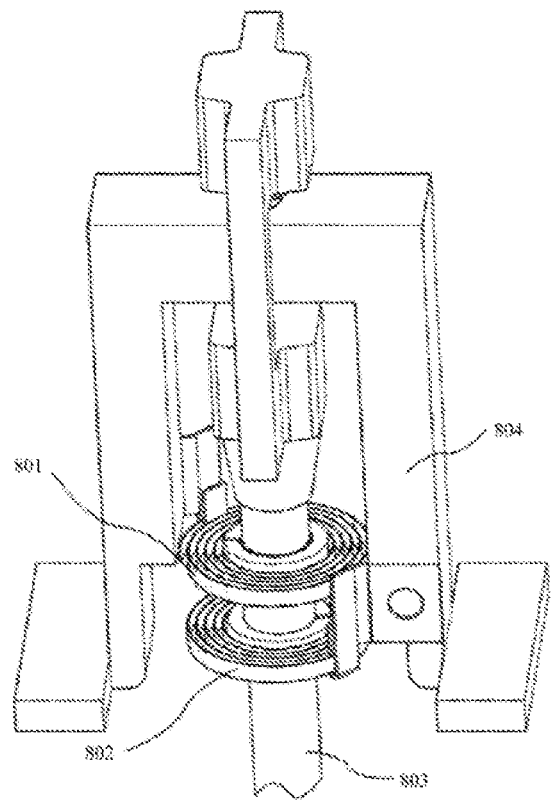
FIG. 8B is a schematic diagram of an apparatus which is used for measuring blood coagulation data and comprises a hair spring as provided by an embodiment of the present invention.

As shown in FIG. 8, the apparatus comprises two hair springs, i.e., a first hair spring 801 and a second hair spring 802, respectively. The inner rings of the first hair spring 801 and the second hair spring 802 are fixedly connected to the outer circumferential surface of the rotary shaft 803, respectively; the outer rings of the first hair spring 801 and the second hair spring 802 are fixedly connected to the fixed support part 804, respectively. The spiral directions of the first hair spring 801 and the second hair spring 802 are opposite.

In an embodiment of the present invention, the apparatus further comprises a sliding guide rail, a sliding part and a motor, wherein the sliding part is connected to the sliding guide rail;

the motor is connected to the sliding part;

the sliding part is connected to the fixed support part; and the motor is configured to receive a control signal, drive the sliding part to slide along the sliding guide rail according to the control signal, and drive the rotary shaft to slide along the sliding guide rail.

In the embodiment of the present invention, after the motor receives the control signal, the motor drives the sliding part to slide along the sliding guide rail. Since the sliding part is connected to the fixed support part, the sliding part drives the fixed support part to slide along the sliding guide rail. Since the fixed support part is fixed to the movable support part by means of the connection part, the fixed support part drives the movable support part to slide along the sliding guide rail. Since the movable support part is fixedly connected to the rotary shaft, the movable support part drives the rotary shaft to slide along the sliding guide rail. As the rotary shaft slides along the sliding guide rail, the rotary shaft may be inserted into or taken out from the measured blood. In this embodiment, the rotary shaft is driven by a motor to move, which is more convenient to use, without a manual operation.

Figure 9:
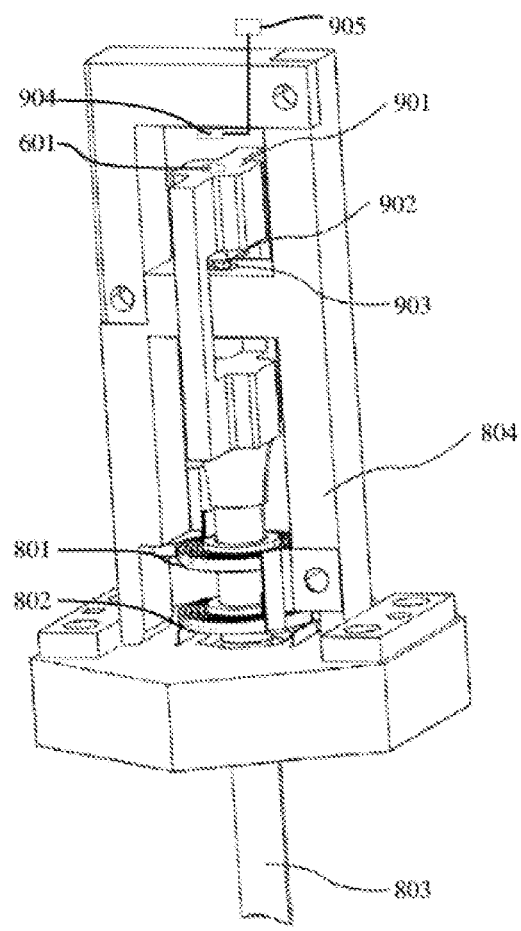
FIG. 9 is a schematic diagram of an apparatus for measuring blood coagulation data as provided by another embodiment of the present invention.

Based on the Hall element shown in FIG. 5, the magnet shown in FIG. 6, and the first hair spring, the second hair spring, the rotary shaft and the fixed support part shown in FIG. 8, the embodiment of the present invention provides an apparatus for measuring blood coagulation data, having a specific structure as shown in FIG. 9.

In order to reduce the frictional force between the fixed support part 804 and the movable support part 901, the fixed support part 804 is connected to the movable support part 901 by means of a top cone 902 and a jewel bearing 903. Specifically, the jewel bearing 903 is fixed on the fixed support part 804. The top cone 902 is fixed on one end of the movable support part 901. The cone top of the top cone 902 is in contact with the jewel bearing 903.

In order to accurately measure the rotation angle of the rotary shaft, and more accurately determine the blood coagulation data of the measured blood, the Hall element 904 is fixedly connected to the fixed support part 804; the movable support part 901 is fixedly connected to the magnet 601, and the Hall element 904 is located in the magnetic field of the magnet 601; the Hall element 904 is connected to the processing unit 905; the Hall element 904 is configured to output a measurement electric signal according to a change in the magnetic field of the magnet 601. The Hall element 904 is implemented by the Hall element shown in FIG. 5, and the magnet 601 is implemented by the magnet shown in FIG. 3. The positional relationship between the Hall element 904 and the magnet 601 is as shown in FIGS. 6 and 7.

In addition, the measurement electric signal here outputted by the Hall element 904 is a Hall voltage $V_H$, and the Hall voltage satisfies Formula II:

$$V_H = \frac{R_H \times I \times B \times \sin\theta}{d}.$$

In order to achieve automatic calibration of the rotary shaft, the apparatus further comprises a first hair spring 801 and a second hair spring 802, wherein the inner rings of the first hair spring 801 and the second hair spring 802 are fixedly connected to the outer circumferential surface of the rotary shaft 803, respectively; the outer rings of the first hair spring 801 and the second hair spring 802 are fixedly connected to the fixed support part 804, respectively. Specifically, as shown in FIG. 8, the spiral directions of the first hair spring 801 and the second hair spring 802 are opposite.

The other end of the movable support part 901 is fixedly connected to the rotary shaft 803. The rotary shaft 803 rotates relative to the fixed support part 804 under the driving force of the measured blood and is able to drive the movable support part 901 to rotate. The movable support part 901 is able to drive the magnet 601 to move to cause a change in the magnetic field of the magnet 601.

A processing unit is specifically configured to determine a rotation angle of the rotary shaft 803 according to the formula I, and determine the blood coagulation data according to the rotation angle. The processing unit 905 may be a microprocessor or an embedded circuit, or the like.

It should be noted that, in the embodiment of the present invention, the Hall element may output a measurement electric signal according to the magnetic induction intensity of the magnet; the measurement electric signal here may be a voltage or a current. When the Hall element is used, the Hall element may be energized for a preset period of time, and after the Hall element is stabilized, it is possible to begin to use the apparatus for measuring the blood coagulation data.

In the embodiment of the present invention, when the apparatus for measuring the blood coagulation data is used, the rotary shaft is placed in a container that contains the measured blood. The container rotates with an external driving force, and the measured blood also rotates with the container. The rotary shaft is driven by the measured blood to rotate relative to the fixed support part, and the rotary shaft drives the movable support part to rotate. The movable support part drives the magnet to rotate. As the magnet rotates, the Hall element measures the magnetic field change of the magnet and outputs a measurement electric signal. The processing unit determines the blood coagulation data of the measured blood according to the measurement electric signal.

The container that contains the measured blood comprises a heating device and is able to heat the measured blood, such that the measured blood is within a preset temperature range, thereby being capable of ensuring that the temperature during the blood coagulation of the measured blood is similar to the body temperature and improving the accuracy of test results.

When determining the blood coagulation data of the measured blood, the processing unit may be specifically configured to determine the rotation angle of the rotary shaft according to the measurement electric signal, and determine the blood coagulation data of the measured blood according to the rotation angle of the rotary shaft.

The magnet in the embodiment of the present invention may include permanent magnet steel, such as NdFeB II magnet steel.

Figure 10:
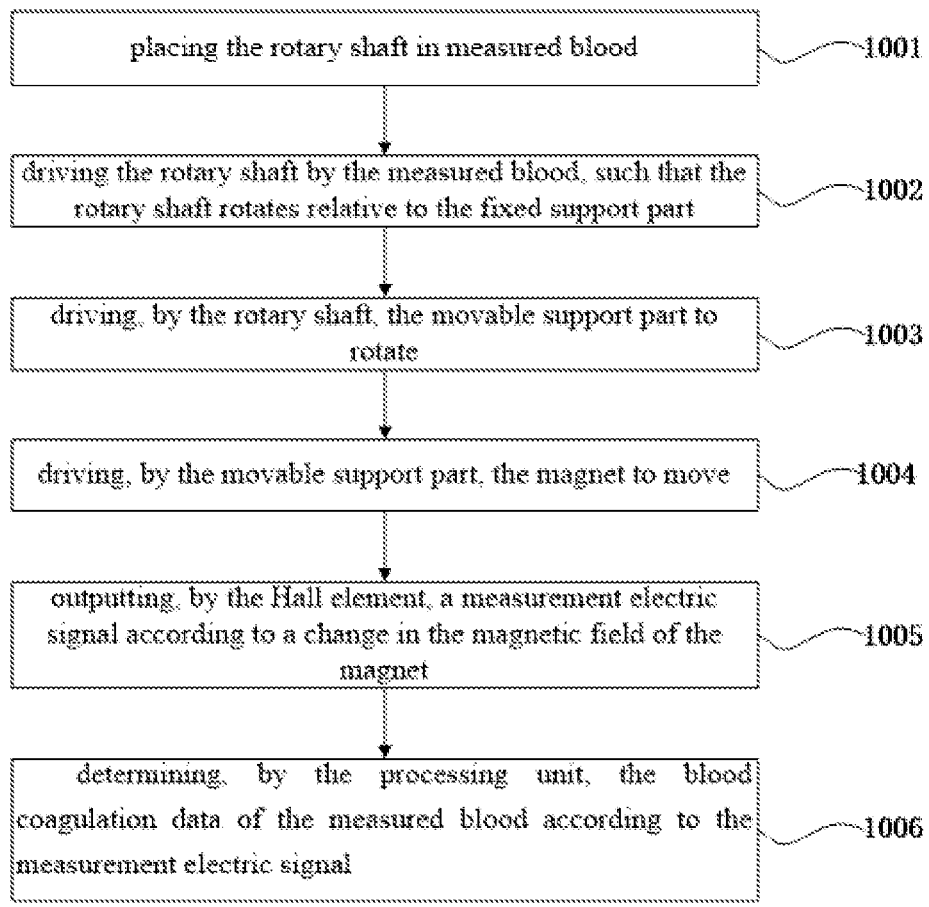
FIG. 10 is a flowchart of a use method of an apparatus for measuring the blood coagulation data as provided by an embodiment of the preset invention.

As shown in FIG. 10, an embodiment of the present invention provides a use method for any apparatus for measuring blood coagulation data according to the embodiment of the present invention, comprising:

Operation 1001: placing the rotary shaft in measured blood;

Operation 1002: driving the rotary shaft by the measured blood, such that the rotary shaft rotates relative to the fixed support part;

Operation 1003: driving, by the rotary shaft, the movable support part to rotate;

Operation 1004: driving, by the movable support part, the magnet to move;

Operation 1005: outputting, by the Hall element, a measurement electric signal according to a change in the magnetic field of the magnet; and Operation 1006: determining, by the processing unit, the blood coagulation data of the measured blood according to the measurement electric signal.

In an embodiment of the present invention, when the apparatus for measuring the blood coagulation data comprises a sliding guide rail, a sliding part and a motor, the operation of placing the rotary shaft in the measured blood includes:

sending a control signal to the motor, such that the motor drives the sliding part to slide along the sliding guide rail according to the control signal, and then a part of the rotary shaft is placed in the measured blood.

Figure 11:
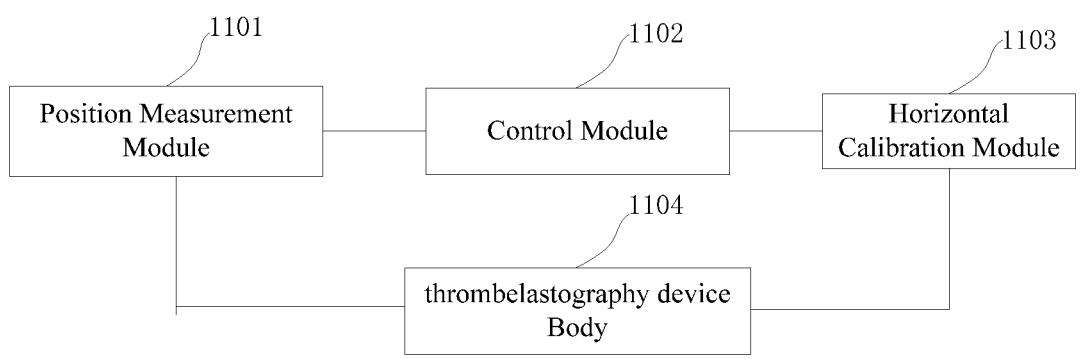
FIG. 11 is a schematic diagram of an apparatus for measuring blood coagulation data as provided by a further embodiment of the present invention.

As shown in FIG. 11, an embodiment of the present invention provides an apparatus for measuring blood coagulation data, comprising a position measurement module 1101, a control module 1102, a horizontal calibration module 1103 and a thrombelastography device body 1104, wherein the position measurement module 1101 is configured to measure a first inclination state of the thrombelastography device body 110, and send information on the first inclination state to the control module 1102;

the control module 1102 is configured to determine whether the thrombelastography device body 1104 is in a horizontal position according to the first inclination state, form a corresponding control instruction according to the first inclination state if the thrombelastography device body is not in the horizontal position, and send the control instruction to the horizontal calibration module 1103; and the horizontal calibration module 1103 is configured to perform horizontal calibration processing on the thrombelastography device body 1104 according to the control instruction.

An embodiment of the present invention provides the apparatus for measuring blood coagulation data. The position measurement module is configured to measure the first inclination state of the thrombelastography device body, and send information representing the first inclination state to the control module. The control module is configured to determine whether the thrombelastography device body is in a horizontal position according to the first inclination state, form a corresponding control instruction according to the first inclination state if the thrombelastography device body is not in the horizontal position, and send the formed control instruction to the horizontal calibration module. The horizontal calibration module is configured to perform horizontal calibration processing on the thrombelastography device body according to the received control instruction. In this way, the position measurement module measures the position where the thrombelastography device body is located, the control module determines whether the thrombelastography device body is in the horizontal position, and the horizontal calibration module performs horizontal calibration processing on the thrombelastography device body according to a determination result from the control module, and automatically completes level measurement and horizontal calibration of the thrombelastography device body, such that the thrombelastography device body can be horizontally calibrated, without the need of methods for manual calibration and manual adjustment.

In the embodiment of the present invention, the control module may be one or more of a processor, a single chip microcomputer, and an integrated circuit, which perform the operations of the control module.

In an embodiment of the present invention, the horizontal calibration module comprises at least one lifting unit. One end of each lifting unit is fixed on the edge of a base of the thrombelastography device body, and the other end of the lifting unit is in contact with a support platform for supporting the thrombelastography device body. Different lifting units are fixed to different positions on the edge of the base. The lifting unit may be extended or shortened according to a control command sent by the control module. When the lifting unit is extended, one side, connected to the lifting unit, of the base ascends; when the lifting unit is shortened, one side, connected to the lifting unit, of the base descends. According to the control instruction sent by the control module, each lifting unit is respectively extended or shortened, such that the edge height of the base for supporting the thrombelastography device body is adjusted. The thrombelastography device body is adjusted to a horizontal position by adjusting an included angle between the base and the horizontal plane. The automatic horizontal calibration of the thrombelastography device body is implemented by the cooperation of the respective lifting units, such that the time required for horizontal calibration is shortened in comparison to manual calibration, and the efficiency of horizontal calibration of the thrombelastography device body is improved.

Figure 12:
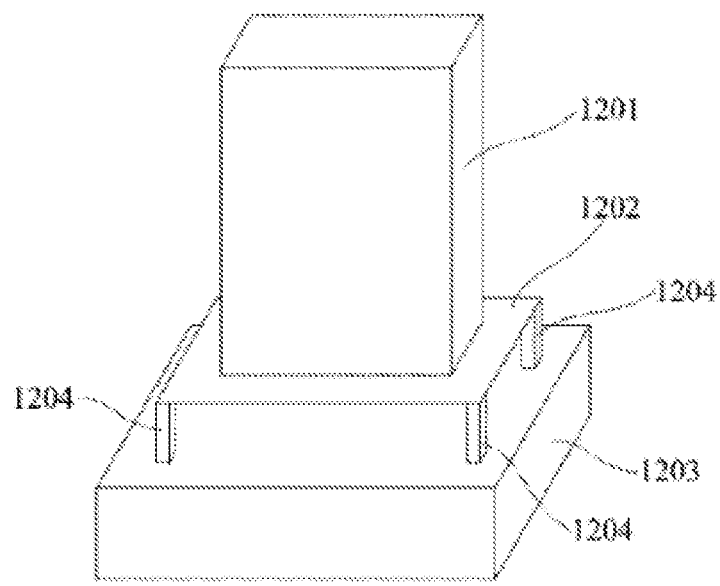
FIG. 12 is a schematic diagram of a horizontal calibration module provided by an embodiment of the present invention.

For example, as shown in FIG. 12, the base 1202 of the thrombelastography device body 1201 is rectangular. The thrombelastography device body 1201 is fixed on the base 1202. Four lifting units 1204 (three of them are marked in FIG. 12) are respectively fixed on four corners of the base 1202. One end of each of the four lifting units 1204 is fixedly connected to the base 1202, and the other end of the lifting unit is in contact with the support platform 1203. When it is required to use the apparatus for measuring blood coagulation data to measure blood coagulation data of blood, the four lifting units 1204 are correspondingly extended or shortened according to a control instruction sent by the control module. When the lifting unit 1204 is extended, one corner, connected to the lifting unit, of the base 1202 ascends; when the lifting unit 1204 is shortened, one corner, connected to the lifting unit, of the base 1202 descends. The thrombelastography device body 1202 fixed on the base 1202 is adjusted to the horizontal position by the cooperation of the four lifting units 1204.

In an embodiment of the present invention, the horizontal calibration unit may comprise one lifting unit only. In this case, the apparatus for measuring blood coagulation data further comprises two fixed fulcrums. One end of each of the two fixed fulcrums is fixed to the edge of the base of the thrombelastography device body, and the other end of the fixed fulcrum is in contact with the support platform for supporting the thrombelastography device body. The two fixed fulcrums and one lifting unit are arranged in a triangle on the base of the thrombelastography device body. The base is supported by two fixed fulcrums and one lifting unit. The lengths of the two fixed fulcrums are fixed. When the apparatus for measuring the blood coagulation data is horizontally calibrated, the two fixed fulcrums are placed in the same horizontal plane, and then, the thrombelastography device body may be horizontally calibrated by one lifting unit. Compared with the horizontal calibration of the thrombelastography device body by means of a plurality of lifting units, the amount of data that needs to be processed is reduced, and the efficiency of horizontal calibration of the thrombelastography device body is improved. In addition, the cost of the apparatus for measuring the blood coagulation data may be reduced by decreasing the number of lifting units.

Figure 13:
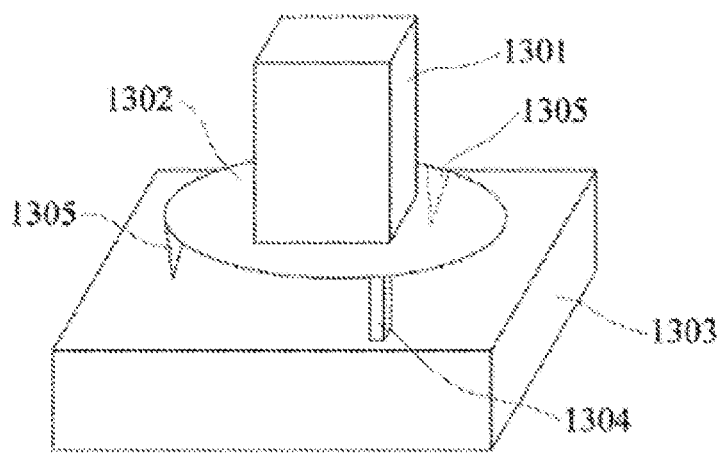
FIG. 13 is a schematic diagram of a horizontal calibration module provided by another embodiment of the present invention.

For example, as shown in FIG. 13, the thrombelastography device body 1301 is fixed on a circular base 1302. Two fixed fulcrums 1305 and one lifting unit 1304 are fixed on the base 1302. One end of each of the two fixed fulcrums 1305 is fixed on the base 1302, and the other end of the fixed fulcrum is in contact with a support platform 1303. One end of the lifting unit 1304 is fixed on the base 1302, and the other end of the lifting unit is in contact with the support platform 1303. The positions where the two fixed fulcrums 1305 and one lifting unit 1304 are located on the base 1302 are three vertices of a triangle. When it is required to use the apparatus for measuring the blood coagulation data to measure blood, the base 1302 is placed on the support platform 1303, and the two fixed fulcrums 1305 are located in the same plane. The lifting unit 1304 is correspondingly extended or shortened according to a control instruction sent by the control module, and the thrombelastography device body 1301 is adjusted to the horizontal position by adjusting an included angle between the base 1302 and the horizontal plane.

In an embodiment of the present invention, the lifting unit may comprise a motor, a screw rod and a nut. The nut is fixed to the edge of the base of the thrombelastography device body. The nut is meshed with the screw rod. One end of the screw rod is fixedly connected to an output shaft of the motor, and the other end of the screw rod is in contact with the support platform. The motor can rotate forwardly or reversely according to a control instruction sent by the control module. The screw rod moves within the nut under the driving force of the motor, such that the edge, where the nut is located, on the base ascends or descends to change the included angle between the base and the horizontal plane, and therefore, the thrombelastography device body is horizontally calibrated.

Figure 14:
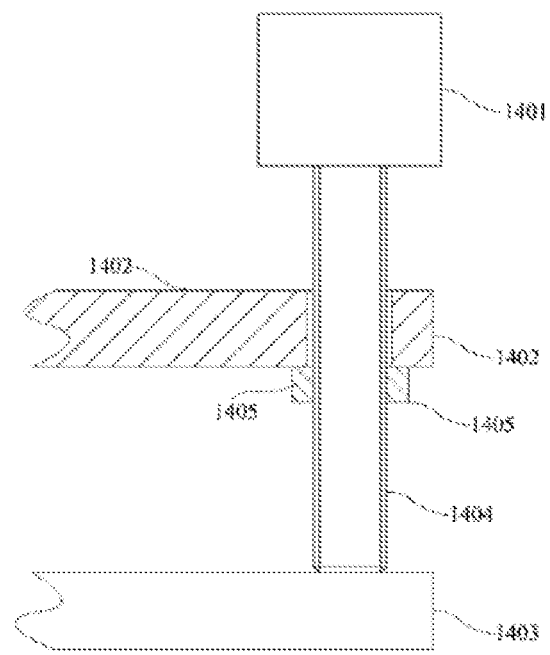
FIG. 14 is a schematic diagram of a lifting unit provided by an embodiment of the present invention.

For example, as shown in FIG. 14, the nut 1405 is fixed to the lower side of the base 1402. The screw rod 1404 is meshed with the nut 1405. The upper end of the screw rod 1404 is fixedly connected to an output shaft of the motor 1401, and the lower end of the screw rod 1404 is in contact with the support platform 1403. The motor 1404 rotates forwardly or reversely according to the control instruction sent by the control module. The screw rod 1404 rotates in the same direction under the driving force of the motor 1401. Due to the meshing effect between the screw rod 1404 and the nut 1405, the screw rod 1404 causes the nut 1405 to ascend or descend in the rotation process, the base 1402 ascends or descends correspondingly under the driving force of the nut 1405, and therefore, the thrombelastography device body fixed on the base 1402 is calibrated horizontally.

In an embodiment of the present invention, the lifting unit may comprise a hydraulic support rod and a hydraulic pump. One end of the hydraulic support rod is fixedly connected to the edge of the base, and the other end of the hydraulic support rod is in contact with the support platform. The hydraulic pump is connected to the hydraulic support rod and supplies power to the hydraulic support rod according to a control instruction sent by the control module. The hydraulic support rod may be extended or shortened under the power of the hydraulic pump, so that the edge of the base ascends or descends to change an included angle between the base and the horizontal plane, and therefore, the thrombelastography device body fixed on the base is calibrated horizontally.

Figure 15:
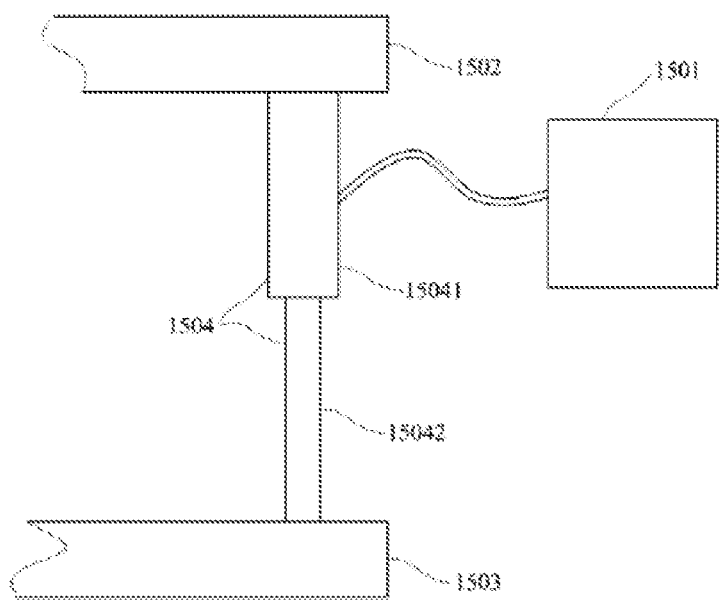
FIG. 15 is a schematic diagram of a lifting unit provided by another embodiment of the present invention.

For example, as shown in FIG. 15, the hydraulic support rod 504 comprises a pressure rod 5041 and a piston rod 5042. The pressure rod 5041 is fixedly connected to the base 502, and the piston rod 5042 is in contact with the support platform 503. The pressure rod 5041 is connected to the hydraulic pump 501. The hydraulic pump 501 can inject hydraulic oil into the pressure rod 5041 or discharge the hydraulic oil from the pressure rod 5041 according to a control instruction sent by the control module. When the hydraulic oil is injected into the pressure rod 5041, the length of the piston rod 5042 outside the pressure rod 5041 increases, and the total length of the hydraulic support rod 504 increases, such that the position, to which the pressure rod 5041 is connected, on the base 502 ascends. When the hydraulic oil in the pressure rod 5041 is discharged, the length of the piston rod 5042 outside the pressure rod 5041 is reduced, and the total length of the hydraulic support rod 504 is reduced, such that the position, to which the pressure rod 5041 is connected, on the base 502 descends. The hydraulic support rod 504 is extended or shortened to adjust the included angle between the base 502 and the horizontal plane, and therefore, the thrombelastography device body fixed on the base 502 is adjusted to a horizontal position.

In an embodiment of the present invention, the position measurement module may be a gyroscope. The gyroscope may be configured to measure an inclination direction and an inclination angle of the thrombelastography device body. An inclination state of the thrombelastography device body may be determined by means of the inclination direction and the inclination angle. Because the gyroscope which may measure the inclination state of the thrombelastography device body has the characteristics of high sensitivity, high precision and the like, the accuracy of the horizontal calibration may be improved.

In an embodiment of the present invention, the apparatus for measuring blood coagulation data may further comprise a vibration measurement module and a data correction module. The position measurement module is configured to measure a first inclination state of the thrombelastography device body before measuring the blood, to measure a second inclination state of the thrombelastography device body during the blood measurement process, and to send the measured second inclination state to the data correction module. The vibration measurement module is configured to measure a vibration state when the thrombelastography device body measures the blood, and send the measured vibration state to the data correction module. The data correction module is configured to correct the blood coagulation data of the blood measured by the thrombelastography device body according to the second inclination state and the vibration state after the thrombelastography device body measures the blood coagulation data of the blood.

Specifically, the vibration measurement module measures a vibration amplitude of the thrombelastography device body by means of a sensor, wherein the measured vibration amplitude ranges from −65535 to +65535, and the data type is an integer or a floating point number. After the vibration measurement module sends the measured vibration amplitude to the data correction module, the data correction module stores a corresponding curve of the vibration amplitude and a standard parameter, wherein the curve is formed by computer calibration.

The data correction module obtains a calibration parameter by calculating the vibration amplitude according to predetermined operation parameters by the following formula (1).

$$P=A*a^2+A*b+c \quad (1)$$

in which, P represents the calibration parameter, A represents the vibration amplitude, a, b and c represent operation parameters, and a, b and c are constants.

After acquiring the calibration parameter, the data correction module corrects the blood coagulation data measured by the thrombelastography device body according to the following formula (2), and obtains the corrected blood coagulation data.

$$X1=X+X*P \quad (2)$$

in which, X1 represents the corrected blood coagulation data, X represents the blood coagulation data measured by the thrombelastography device body, and P represents the calibration parameter calculated by the above formula (1).

The thrombelastography device body has a certain inclination angle during the operating process, and the rotation of the measured blood may cause a certain vibration of the thrombelastography device body. The vibration and inclination of the thrombelastography device body will have certain influences on the measured blood coagulation data. By measuring the inclination state and the vibration state during the operation process of the thrombelastography device body, the measured blood coagulation data is corrected according to the inclination state and the vibration state, thereby eliminating or reducing the error caused by the inclination or vibration of the thrombelastography device body, and improving the measurement accuracy of blood coagulation data of blood.

Figure 16:
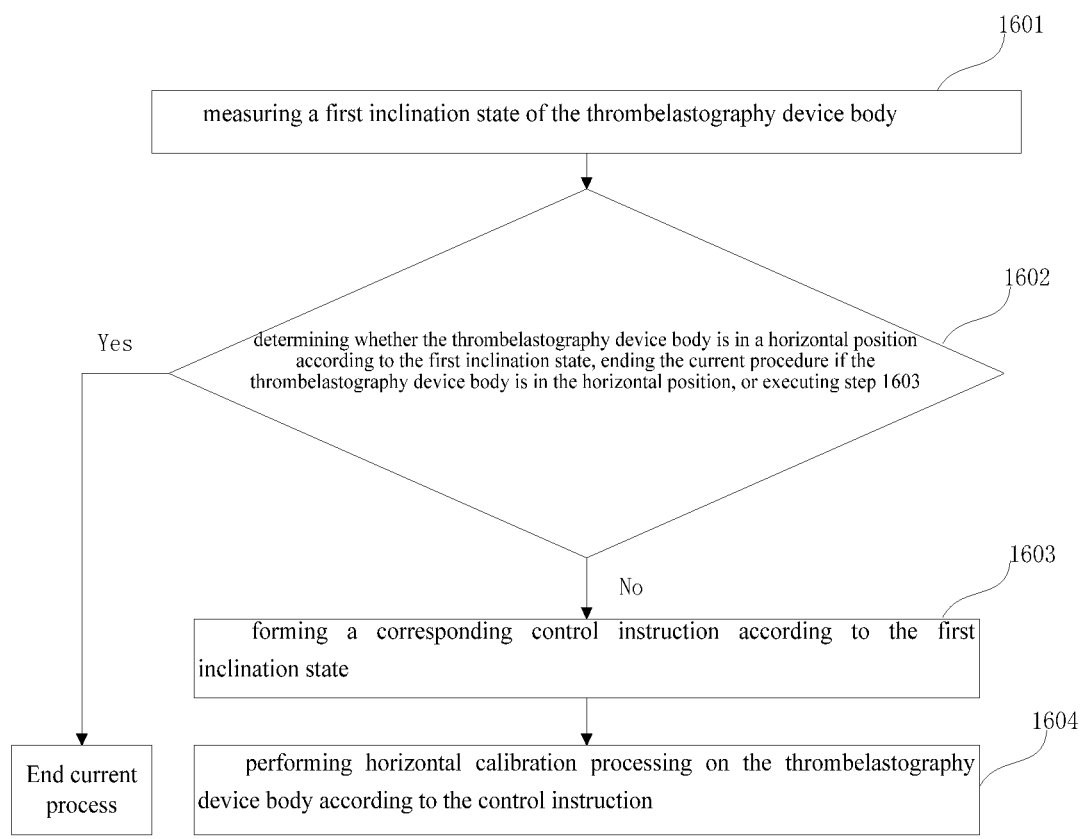
FIG. 16 is a flowchart of a method for calibrating the apparatus for measuring blood coagulation data as provided by an embodiment of the present invention.

As shown in FIG. 16, an embodiment of the present invention provides a calibration method for an apparatus for measuring blood coagulation data, comprising:

Operation 1601: measuring a first inclination state of the thrombelastography device body;

Operation 1602: determining whether the thrombelastography device body is in a horizontal position according to the first inclination state, ending the current procedure if the thrombelastography device body is in the horizontal position, or executing step 1603;

Operation 1603: forming a corresponding control instruction according to the first inclination state; and Operation 1604: performing horizontal calibration processing on the thrombelastography device body according to the control instruction.

According to the calibration method for the apparatus for measuring the blood coagulation data as provided by the embodiment of the present invention, the first inclination state of the thrombelastography device body is measured before the blood is measured by the apparatus for measuring the blood coagulation data; whether the thrombelastography device body is in the horizontal position is determined according to the first inclination state, wherein the blood may be measured by the apparatus for measuring the blood coagulation data directly if the thrombelastography device body is in the horizontal position, and the corresponding control instruction is formed according to the first inclination state if the thrombelastography device body is not in the horizontal position; and the thrombelastography device body is subjected to horizontal calibration processing according to the control instruction. In this way, the inclination state measurement and horizontal calibration of the thrombelastography device body can be automatically completed, such that the thrombelastography device body is horizontally calibrated, without manual measurement and manual adjustment.

In an embodiment of the present invention, when the thrombelastography device body is subjected to horizontal calibration processing according to the control instruction, the edge of the base of the thrombelastography device body ascends or descends according to the control instruction to adjust an included angle between the base of the thrombelastography device body and the horizontal plane, and therefore, the thrombelastography device body fixed on the base is adjusted to the horizontal position. By means of such calibration manner, a variety of structures may be used to adjust the included angle between the base of the thrombelastography device body and the horizontal plane, thereby improving the applicability of the calibration method. By adjusting the edge position of the base, the force required to adjust the included angle between the base and the horizontal plane may be reduced, such that a smaller power device can be used, thereby reducing the volume of the entire apparatus for measuring blood coagulation data, and improving the convenience of carrying the apparatus for measuring the blood coagulation data.

In an embodiment of the present invention, the inclination state and the vibration state of the thrombelastography device body are measured when the thrombelastography device body measures the blood coagulation of blood. After the blood coagulation data of blood is measured by the thrombelastography device body, the measured blood coagulation data is corrected according to the inclination state and the vibration state which are obtained during the measurement process, thereby eliminating or reducing the error caused by the inclination or vibration of the thrombelastography device body and improving the measurement accuracy of the blood coagulation.

Figure 17:
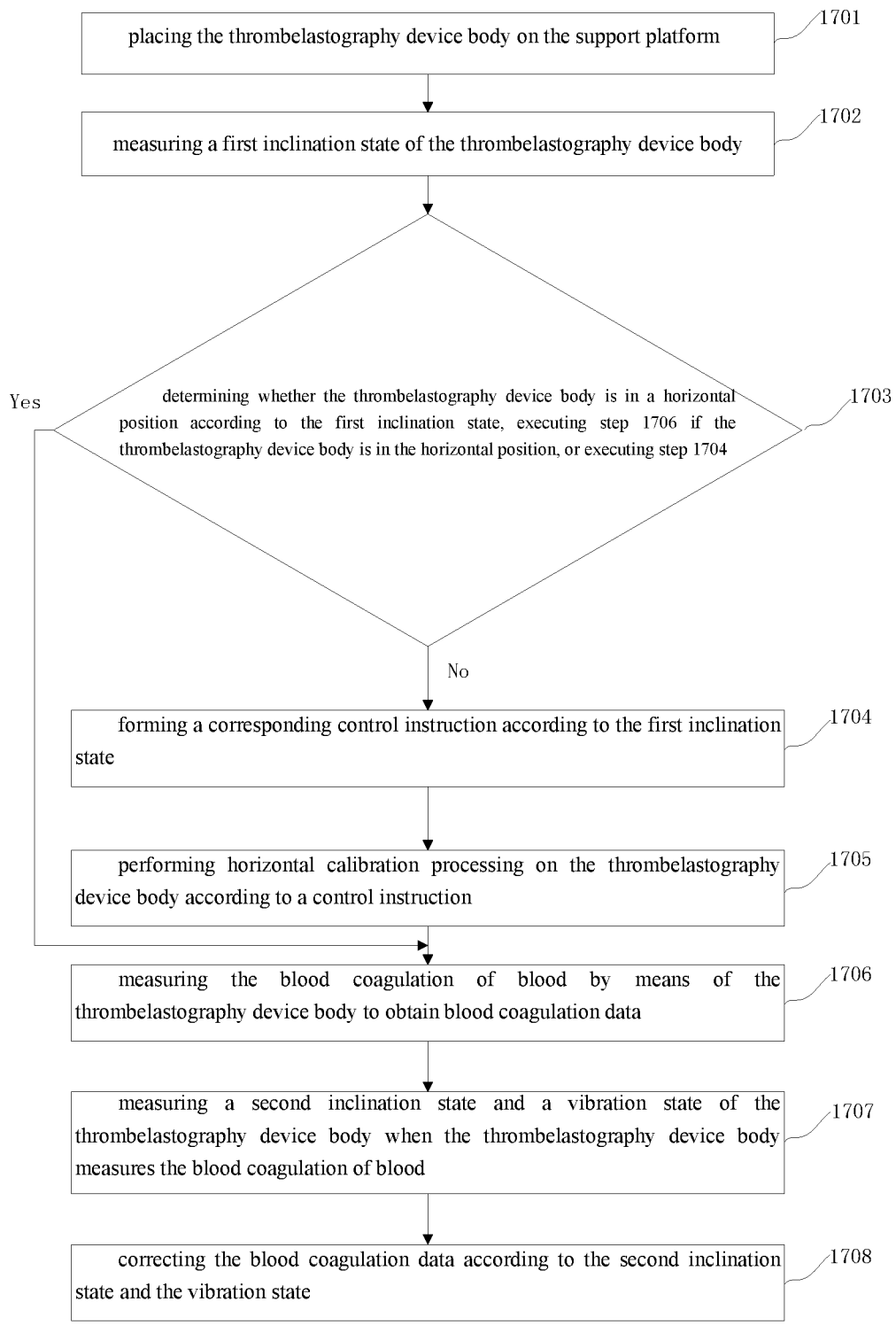
FIG. 17 is a flowchart of a method for calibrating the apparatus for measuring blood coagulation data as provided by another embodiment of the present invention.

In order to make the structure of the apparatus for measuring blood coagulation data and the calibration method thereof as provided by the embodiment of the present invention more clear, the calibration method provided by the embodiment of the present invention is further described in detail below with reference to the structure of the apparatus for measuring blood coagulation data shown in FIG. 13. Referring to FIG. 17, the method comprises the operations 1701-1708:

Operation 1701: placing the thrombelastography device body on the support platform.

In an embodiment of the present invention, when the blood coagulation of blood needs to be measured by the apparatus for measuring the blood coagulation data, the base of the thrombelastography device body is placed on the support platform, and the thrombelastography device body is also located on the support platform under the support of the base. In the course of placing the base, two fixed fulcrums fixed on the base are located on the same horizontal plane by adjusting the position of the base on the support platform.

For example, as shown in FIG. 13, the base 1302 is placed on the support platform 1303. By adjusting the position of the base 1302 or horizontally rotating the base 1302, the points on the two fixed fulcrums 1305, which are in contact with the support platform 1303, are located on the same horizontal plane.

Operation 1702: measuring a first inclination state of the thrombelastography device body.

In an embodiment of the present invention, after the base of the thrombelastography device body is placed on the support platform, the position measurement module measures the first inclination state of the thrombelastography device body, wherein the first inclination state includes an inclination direction and an inclination angle of the thrombelastography device body relative to the horizontal plane. After the first inclination state of the thrombelastography device body is measured, the obtained first inclination state is sent to the control module.

For example, a gyroscope which serves as the position measurement module is fixed on the thrombelastography device body. The gyroscope may measure the inclination direction and the inclination angle of the thrombelastography device body, and send the measured inclination direction and inclination angle to the control module as the first inclination state.

Operation 1703: determining whether the thrombelastography device body is in a horizontal position according to the first inclination state, executing step 1706 if the thrombelastography device body is in the horizontal position, or executing step 1704.

In an embodiment of the present invention, after receiving the first inclination state sent by the position measurement module, the control module determines whether the inclination angle included in the first inclination state is zero. If the inclination angle is zero, it is indicated that the thrombelastography device body is not inclined and located in the horizontal position, thereby being free of calibration, and correspondingly, operation 1706 is then performed. If the inclination angle is not zero, it is indicated that the thrombelastography device body is inclined and needs to be horizontally calibrated, and correspondingly, operation 1704 is then executed.

Operation 1704: forming a corresponding control instruction according to the first inclination state.

In an embodiment of the present invention, after it is determined that the thrombelastography device body inclines, according to the inclination direction and the inclination angle included in the first inclination state, a corresponding strategy for adjusting the thrombelastography device body is obtained by a pre-formed model, and the obtained strategy is sent as a control instruction to a horizontal calibration unit.

Operation 1705: performing horizontal calibration processing on the thrombelastography device body according to a control instruction.

In an embodiment of the present invention, after the horizontal calibration unit receives the control instruction, each lifting unit included in the horizontal calibration unit is extended or shortened according to the control instruction to adjust the included angle between the base of the thrombelastography device body and the horizontal plane, such that the thrombelastography device body is adjusted to the horizontal position. During the process in which the lifting unit is extended or shortened according to the control instruction, the position measurement module measures a position state of the thrombelastography device body in real time, the control module correspondingly updates the control instruction in real time, and finally the thrombelastography device body is calibrated to the horizontal position.

For example, as shown in FIG. 13, if the lifting unit 1304 is of the structure shown in FIG. 14, the motor 1401 rotates forwardly or reversely according to a control instruction, such that the relative positions of the nut 1405 and the screw rod 1404 are changed to cause the base 1402 ascend or descend, and the thrombelastography device body is then calibrated to the horizontal position; if the lifting unit 1304 is of the structure shown in FIG. 15, the hydraulic pump 1501 charges pressure to or releases pressure from the pressure rod 15041 according to a control instruction to change the total length of the hydraulic support rod 1504, such that the base 1502 ascends or descends, and therefore the thrombelastography device body is calibrated to the horizontal position.

Operation 1706: measuring the blood coagulation of blood by means of the thrombelastography device body to obtain blood coagulation data.

In an embodiment of the present invention, after the thrombelastography device body is calibrated to the horizontal position, the blood coagulation is measured by means of the thrombelastography device body to obtain the blood coagulation data of blood.

Operation 1707: measuring a second inclination state and a vibration state of the thrombelastography device body when the thrombelastography device body measures the blood coagulation of blood.

In an embodiment of the present invention, during the process in which the thrombelastography device body measures the blood coagulation of blood, the rotation of the blood will cause an impact on the thrombelastography device body. Under the impact, the thrombelastography device body will incline at a certain angle and vibrate to a certain degree. The second inclination state during the process in which the thrombelastography device body measures the blood coagulation of blood is measured by means of the position measurement module. The vibration state during the process in which the thrombelastography device body measures the blood coagulation of blood is measured by means of the vibration measurement module. The obtained second inclination state and vibration state are sent to the data correction module.

Operation 1708: correcting the blood coagulation data according to the second inclination state and the vibration state.

In an embodiment of the present invention, after the thrombelastography device body measures the blood coagulation data, the data correction module corrects the blood coagulation data measured by the thrombelastography device body according to the second inclination state and the vibration state of the thrombelastography device body during the blood coagulation measurement process by a pre-formed correction model, thereby eliminating the influences on the inclination and vibration of the thrombelastography device body and measurement results.

Figure 18:
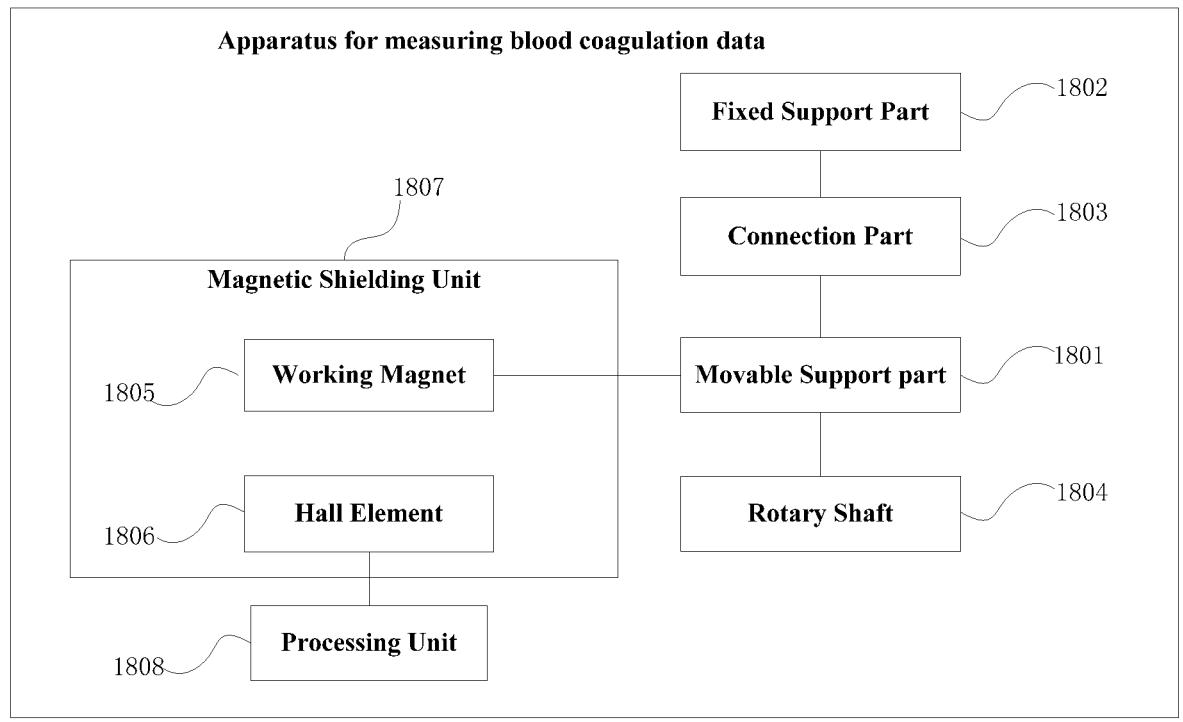
FIG. 18 is a schematic diagram of an apparatus which is used for measuring blood coagulation data and comprises a magnetic shielding unit as provided by an embodiment of the present invention.

In an embodiment of the present invention, on the basis of the apparatus for measuring blood coagulation data shown in FIG. 1, the apparatus for measuring blood coagulation data may further comprise a magnetic shielding unit. The apparatus for measuring blood coagulation data, which comprises the magnetic shielding unit, is as shown in the FIG. 18, comprises a movable support part 1801, a fixed support part 1802, a connection part 1803, a rotary shaft 1804, a magnet 1805, a Hall element 1806, a magnetic shielding unit 1807, and a processing unit 1808. The Hall element 1806 and the magnet 1805 are located inside the magnetic shielding unit 1807.

One end of the movable support part is fixedly connected to the rotary shaft, and the other end of the movable support part is connected to the fixed support part by means of the connection part;

the movable support part is fixedly connected to the magnet;

the rotary shaft is able to rotate relative to the fixed support part under the driving force of measured blood and drive the movable support part to rotate;

the movable support part is able to move the magnet to cause a change in the magnetic field of the magnet;

the Hall element is connected to the processing unit;

the magnetic shielding unit is configured to shield the influences of an external magnetic field on the Hall element and the magnet;

the Hall element is used for outputting a measurement electric signal according to the magnetic field change of the magnet; and the processing unit is used for determining blood coagulation data of the measured blood according to the measurement electric signal.

In the embodiment of the present invention, the rotary shaft rotates relative to the fixed support part under the driving force of the measured blood and drives the movable support part to rotate. The movable support part drives the magnet to move to cause a change in the magnetic field of the magnet. The Hall element outputs the measurement electric signal according to the magnetic field change of the magnet. The processing unit determines the blood coagulation data of the measured data according to the measurement electric signal. The magnetic shielding unit shields the influences to the external magnetic field on the Hall element and the magnet, such that the magnetic field change of the magnet, which is measured by the Hall element, reflects the blood coagulation data more accurately, the processing unit obtains more accurate blood coagulation data, and the measurement accuracy of the measured blood is improved.

In order to provide the Hall element inside the magnetic shielding unit conveniently, in an embodiment of the present invention, the apparatus further comprises a first connection rod, wherein the magnetic shielding unit is provided with a first via hole; and one end of the first connection rod is fixedly connected to the fixed support part, and the other end of the first connection rod passes through the first via hole of the magnetic shielding unit, extends into the magnetic shielding unit and is fixedly connected to the Hall element.

In this embodiment, since the Hall element extends into the magnetic shielding unit by means of the first connection rod, the magnetic shielding unit has a better effect of protecting the Hall element away from the influences from the external magnetic field. In addition, the Hall element is fixedly connected to the fixed support part by means of the first connection rod. Since the Hall element is stationary, when the magnet moves along with the movable support part, the Hall element may more accurately measure the magnetic field change of the magnet.

In order to provide the magnet inside the magnetic shielding unit conveniently, in an embodiment of the present invention, the apparatus further comprises a second connection rod, wherein the magnetic shielding unit is provided with a second via hole; and one end of the second connection rod is fixedly connected to the movable support part, and the other end of the second connection rod passes through the second via hole of the magnetic shielding unit, extends into the magnetic shielding unit and is fixedly connected to the magnet.

In this embodiment, since the magnet extends into the magnetic shielding unit by means of the second connection rod, the magnetic shielding unit has a better effect of protecting the magnet away from the influences from the external magnetic field, such that the Hall element can more accurately measure the magnetic field change of the magnet.

In an embodiment of the present invention, the magnetic shielding unit comprises a support cylinder and a shielding layer, wherein the shielding layer is formed by winding a metal conductive shielding tape on the support cylinder.

In this embodiment, the magnetic shielding unit is cylindrical, and the Hall element and the magnet may be provided inside the support cylinder. A first cover body and a second cover body may be respectively provided at two ends of the support cylinder, wherein the first cover body is provided with a first via hole, the second cover body is provided with a second via hole, and the first cover body and the second cover body are respectively wound with the metal conductive shielding tape. Therefore, the correlation of the magnetic shielding unit to shield the external magnetic field can be made better.

The metal conductive shielding tape comprises an aluminum conductive shielding tape, a copper conductive shielding tape, a tinned copper conductive shielding tape.

In an embodiment of the present invention, the magnetic shielding unit comprises a magnetic shielding mesh cover made of a ferromagnetic material, and a box body made of a ferromagnetic material.

The ferromagnetic material includes the following components selected from a group consisting of iron, copper, aluminum, soft iron, silicon steel, permalloy, and the like.

The higher the magnetic permeability of the ferromagnetic material and the larger the cross-sectional area of a magnetic circuit, the smaller the magnetic resistance of the magnetic circuit, the larger the magnetic flux concentrated in the magnetic circuit, and the leakage flux in air is greatly reduced. Therefore, the ferromagnetic material acts as a magnetic field shield by concentrating magnetic lines of a disturbance source.

In addition, the magnetic shielding mesh cover made of the ferromagnetic material and the box body made of the ferromagnetic material may be made by argon arc welding. Since no filler is used in the argon arc welding process, the magnetic conduction continuity of the magnetic shielding mesh cover made of the ferromagnetic material and the box body made of the ferromagnetic material can be maintained.

Figure 19:
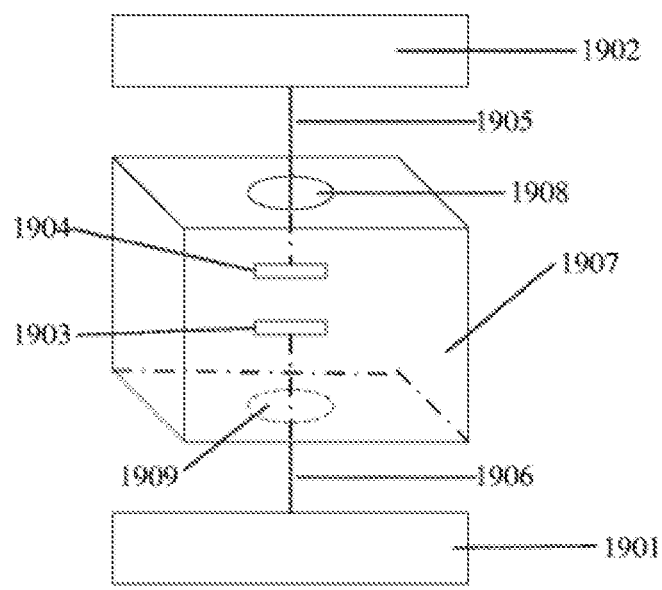
FIG. 19 is a schematic diagram of a connection relationship of a magnetic shielding unit provided by an embodiment of the present invention.

As shown in FIG. 19, the embodiment of the present invention provides a partial schematic diagram of an apparatus for measuring the blood coagulation data. The apparatus comprises: a movable support part 1901, a fixed support part 1902, a magnet 1903, a Hall element 1904, a first connection rod 1905, a second connection rod 1906 and a magnetic shielding unit, wherein the magnetic shielding unit is a box body 1907 made of a ferromagnetic material, the box body 1907 made of the ferromagnetic material is provided with a first via hole 1908 and a second via hole 1909;

one end of the first connection rod 1905 is fixedly connected to the fixed support part 1902, and the other end of the first connection rod 1905 passes through the first via hole 1908 in the box body 1907, extends into the box body 1907 and is fixedly connected to the Hall element 1904;

one end of the second connection rod 1906 is fixedly connected to the movable support part 1902, and the other end of the second connection rod 1906 passes through the second via hole 1909 in the box body 1907, extends into the box body 1907 and is fixedly connected to the magnet 1903.

The first connection rod and the second connection rod are both made of a rigid material.

In an embodiment of the present invention, an N pole and an S pole of the magnet are located on the same plane.

Specifically, when the magnet is in a shape of a disk, the N pole of the magnet is semicircular, and the S pole of the magnet is semicircular. When the magnet is in a shape of a strip, the N pole of the magnet is a half of the strip, and the S pole of the magnet is a half of the strip.

In an embodiment of the present invention, the magnet is annular, and the N and S poles are evenly spaced apart on the magnet.

In addition, in order to enable the Hall element to more accurately measure the change in the magnetic field of the magnet, the surface of the magnet is parallel to the surface of the Hall element.

In an embodiment of the present invention, the processing unit is configured to determine a rotation angle of the rotary shaft according to the amplitude of the measurement electric signal and Formula I, and determine the blood coagulation data of the measured blood according to the rotation angle;

wherein the formula 1 is: $W=D\times I$, where W is the rotation angle, I is the amplitude of the measurement electric signal, and D is a proportional coefficient of the amplitude of the measurement electric signal and the rotation angle.

In the embodiment of the present invention, the measurement electric signal may be a voltage or a current; the proportional coefficient D of the amplitude of the measurement electric signal and the rotation angle may be summarized according to historical data of the amplitude of the measurement electric signal and the corresponding rotation angle, or may be empirically obtained.

Figure 20:
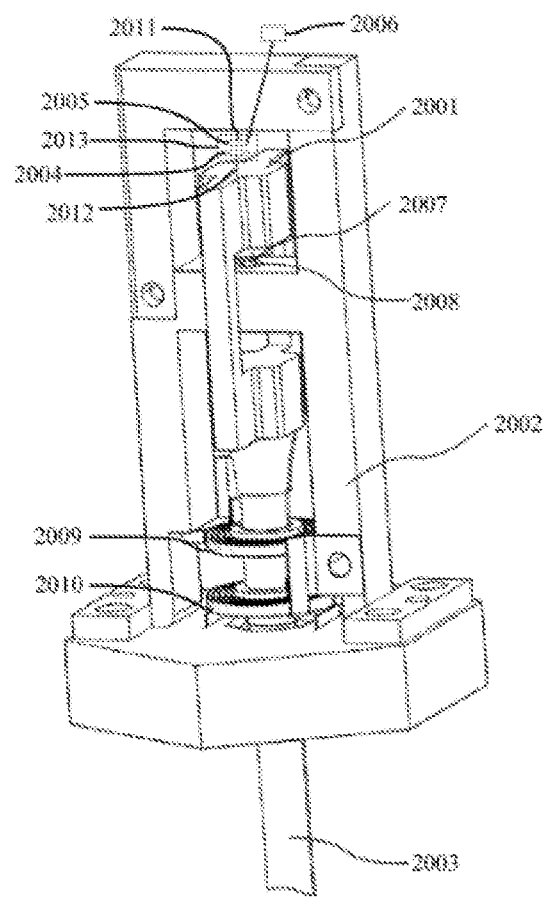
FIG. 20 is a schematic diagram of an apparatus which is used for measuring blood coagulation data and comprises a magnetic shielding unit as provided by another embodiment of the present invention.

As shown in FIG. 20, an embodiment of the present invention provides an apparatus for measuring blood coagulation data, comprising:

a movable support part 2001, a fixed support part 2002, a connection part, a rotary shaft 2003, a magnet 2004, a Hall element 2005, a processing unit 2006, a first hair spring 2009, a second hair spring 2010, a first connection rod 2011, a second connection rod 2012 and a magnetic shielding unit, wherein the connection part comprises a top cone 2007 and a jewel bearing 2008;

the jewel bearing 2008 is fixed on the fixed support part 2002; the top cone 2007 is fixed on the movable support part 2001; the top cone 2007 is connected to the jewel bearing 2008 in a form of point contact;

one end of the movable support part 2001 is fixedly connected to the rotary shaft 2003; the magnetic shielding unit is a box body 2013 made of a ferromagnetic material;

the box body 2013 is provided with a first via hole and a second via hole;

one end of the first connection rod 2011 is fixedly connected to the fixed support part 2002, and the other end of the first connection rod 2011 passes through the first via hole of the box body 2013, extends into the box body 2013 and is fixedly connected to the Hall element 2005;

one end of the second connection rod 2012 is fixedly connected to the movable support part 2001, and the other end of the second connection rod 2012 passes through the second via hole of the box body 2013, extends into the box body 2013 and is fixedly connected to the magnet 2004;

inner rings of the first hair spring 2009 and the second hair spring 2010 are fixedly connected to an outer circumferential surface of the rotary shaft 2003 respectively;

outer rings of the first hair spring 2009 and the second hair spring 2010 are fixedly connected to the fixed support part respectively;

the first hair spring 2009 and the second hair spring 2010 are both configured to, after the rotary shaft 2003 rotates away from a balanced position, generate an acting force for rotating the rotary shaft 2003 towards the balanced position.

The rotary shaft 2003 rotates relative to the fixed support part 2002 under the driving force of the measured blood and drives the movable support part 2001 to rotate;

the movable support part 2001 drives the magnet 2004 to rotate; the Hall element 2005 is connected to the processing unit 2006;

a box body 2013 is configured to shield the influence of an external magnetic field on the Hall element 2005 and the magnet 2004;

a Hall element 2005 is configured to output a measurement electric signal according to a change in the magnetic field of the magnet 2004; and the processing unit 2006 is configured to determine blood coagulation data of the measured blood according to the measurement electric signal.

The N pole and the S pole of the magnet 2004 are located on the same plane. The spiral directions of the first hair spring 2009 and the second hair spring 2010 are opposite. The magnetic shielding unit may be fixed on the fixed support part.

In the embodiment of the present invention, the Hall element may output a measurement electric signal according to the magnetic induction intensity of the magnet; the measurement electric signal here may be voltage or current. When the Hall element is used, the Hall element may be energized for a preset period of time first, and after the Hall element is stabilized, it is possible to begin to use the apparatus for measuring blood coagulation data.

In the embodiment of the present invention, when the apparatus for measuring the blood coagulation data is used, the rotary shaft is placed in a container that contains the measured blood. The container rotates with an external driving force, and the measured blood also rotates with the container. The rotary shaft is driven by the measured blood to rotate relative to the fixed support part, and the rotary shaft drives the movable support part to rotate. The movable support part drives the magnet to rotate. The body box shields the influences of the external magnetic field on the Hall element and the magnet. As the magnet rotates, the Hall element measures the magnetic field change of the magnet and outputs a measurement electric signal. The processing unit determines the blood coagulation data of the measured blood according to the measurement electric signal.

The container that contains the measured blood comprises a heating device and is able to heat the measured blood, such that the measured blood is within a preset temperature range, thereby being capable of ensuring that the temperature during the blood coagulation of the measured blood is similar to the body temperature and improving the accuracy of test results.

When determining the blood coagulation data of the measured blood, the processing unit may be specifically configured to determine a rotation angle of the rotary shaft according to the measurement electric signal, and determine the blood coagulation data of the measured blood according to the rotation angle of the rotary shaft.

The magnet in the embodiment of the present invention may include permanent magnet steel, such as NdFeB II magnet steel.

In the embodiment of the present invention, the box body is made of a ferromagnetic material. The magnetic permeability of the ferromagnetic material is several thousand times greater than the magnetic permeability of air, but the magnetic reluctance of a cavity is much larger than that of the ferromagnetic material. The vast majority of magnetic lines of the external magnetic field will pass through the walls of the box body, but a small amount of magnetic fluxes enter into the box body. In this way, there is substantially no external magnetic field in the cavity inside the box body, so as to shield the external magnetic field. After the external magnetic field is shielded by the box body, the magnetic field change measured by the Hall element is not disturbed by the external magnetic field, so that the measurement result is more accurate, and the blood coagulation data determined by the processing unit is more accurate.

Figure 21:
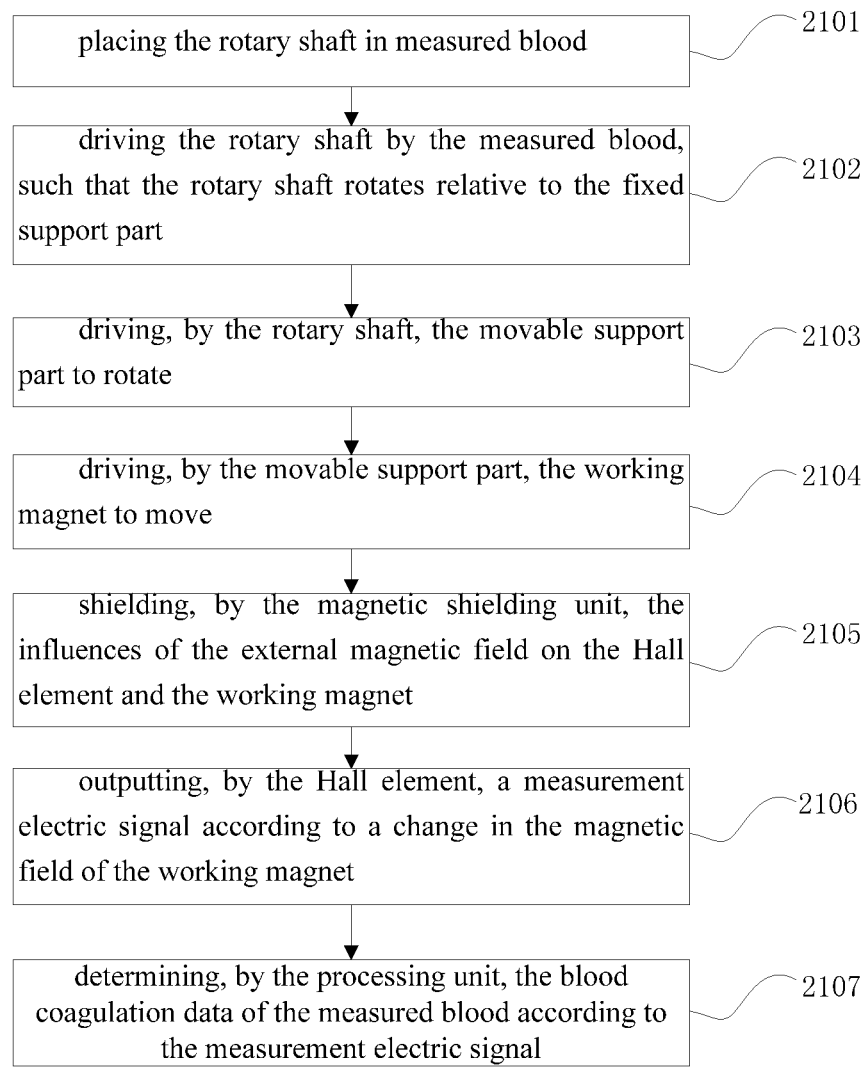
FIG. 21 is a flowchart of a use method for an apparatus which is used for measuring blood coagulation data and comprises a magnetic shielding unit as provided by an embodiment of the present invention.

When the apparatus for measuring blood coagulation data comprises a magnetic shielding unit, on the basis that the embodiment of the present invention provides a use method for the apparatus for measuring blood coagulation data, based on the steps shown in FIG. 10, an operation of shielding external magnetic fields of the Hall element and the magnet by means of the magnetic shielding unit, specially as shown in FIG. 21, includes:

Operation 2101: placing the rotary shaft in measured blood;

Operation 2102: driving the rotary shaft by the measured blood, such that the rotary shaft rotates relative to the fixed support part;

Operation 2103: driving, by the rotary shaft, the movable support part to rotate;

Operation 2104: driving, by the movable support part, the magnet to move;

Operation 2105: shielding, by the magnetic shielding unit, the influences of the external magnetic field on the Hall element and the magnet;

Operation 2106: outputting, by the Hall element, a measurement electric signal according to a change in the magnetic field of the magnet; and Operation 2107: determining, by the processing unit, the blood coagulation data of the measured blood according to the measurement electric signal.

Various embodiments of the present invention have at least the following beneficial effects:

1. In the embodiment of the present invention, the rotary shaft is able to rotate relative to the fixed support part under the driving force of measured blood and drive the movable support part to rotate; the movable support part is able to move the magnet to cause a change in the magnetic field of the magnet; the Hall element is used for outputting a measurement electric signal according to the magnetic field change of the magnet; and the processing unit is used for determining blood coagulation data of the measured blood according to the measurement electric signal. The Hall element has good stability and high precision and improves the measurement accuracy of the blood coagulation data.

2. In the embodiment of the present invention, the frictional force between the movable support part and the fixed support part is reduced by a rolling bearing, and the influence of the frictional force on the rotation of the movable support part is reduced, thereby reducing the influence of the frictional force on the magnetic field change of the magnet, so that the magnetic field change of the magnet which has good stability and high precision more accurately reflects the blood coagulation data of the measured blood.

3. In the embodiment of the present invention, the rotary shaft rotates relative to the fixed support part under the driving force of the measured blood and drives the movable support part to rotate. The movable support part rotates with the connection part as an axis. In the connection part, since the contact area between the top cone and the jewel bearing is relatively small, the frictional force between the top cone and the jewel bearing is relatively small. When the movable support part rotates with the rotary shaft, the frictional force has less resistance to the rotation, thereby reducing the influence of the frictional force on the magnetic field change of the magnet, so that the magnetic field change of the magnet more accurately reflects the blood coagulation data of the measured blood.

4. In the embodiment of the present invention, the movable support part is supported by the interactive force between the first magnet and the second magnet. The movable support part suspends by using the magnetic force generated between the first magnet and the second magnet. There is no contact between the first magnet and the second magnet, and therefore no frictional force exists. The rotary shaft rotates relative to the fixed support part under the driving force of the measured blood and drives the movable support part to rotate. The movable support part rotates under the action of a magnetic force generated between the first magnet and the second magnet of the connection part. In the connection part, there is no frictional force between the first magnet and the second magnet, thereby having less resistance to the rotation of the movable support part, such that the magnetic field change of the magnet more accurately reflects the blood coagulation data of the measured blood.

5. In the embodiment of the present invention, the blood coagulation data of the measured blood is determined according to the measurement electric signal outputted by the Hall element. Different from a resistor that will rise in temperature during use and makes the measurement result inaccurate, the Hall element has good stability and high precision. The measurement electric signal is outputted according to the rotation angle of the rotary shaft. The processing unit determines the blood coagulation data of the measured blood according to the measurement electric signal, and therefore, the measured blood can be measured more accurately.

6. In the embodiment of the present invention, the position measurement module is configured to measure the first inclination state of the thrombelastography device body, and send information on the measured first inclination state to the control module. The control module is configured to determine whether the thrombelastography device body is in a horizontal position according to the received first inclination state, form a corresponding control instruction according to the first inclination state if the thrombelastography device body is not in the horizontal position, and send the control instruction to the horizontal calibration module. The horizontal calibration module is configured to perform horizontal calibration processing on the thrombelastography device body according to the received control instruction. In this way, the position measurement module measures the position where the thrombelastography device body, is located, the control module determines whether the thrombelastography device body is in a horizontal position, and the horizontal calibration module performs horizontal calibration processing on the thrombelastography device body according to a judgment result of the control module, and automatically completes level measurement and horizontal calibration of the thrombelastography device body, such that the thrombelastography device body can be horizontally calibrated, without the need of methods for manual calibration and manual adjustment.

7. In an embodiment of the present invention, two fixing fulcrums and one lifting unit are fixed on a bracket of the thrombelastography device body. The lengths of the two fixed fulcrums are fixed. After the two fixed fulcrums are placed in the same horizontal plane, the thrombelastography device body may be horizontally calibrated by one lifting unit, such that the amount of data that needs to be processed is reduced, and the time required for horizontally calibrating the thrombelastography device body is further shortened. In addition, the cost of the device for measuring the blood coagulation data may be reduced by decreasing the number of lifting units.

8. In the embodiment of the present invention, the lifting unit may comprise a motor, a screw rod and a nut, or may comprise a hydraulic support rod and a hydraulic pump. Therefore, the lifting unit has a plurality of different implementation structures which can be flexibly selected according to requirements during the business implementation process, thereby improving the applicability of the apparatus for measuring blood coagulation data.

9. In the embodiment of the present invention, the position measurement module can be implemented by a gyroscope. Because the gyroscope has the characteristics of high sensitivity and high precision, the inclination state of the thrombelastography device body can be measured by the gyroscope, and therefore the accuracy of the horizontal calibration can be improved.

10. In the embodiment of the present invention, in the process of measuring the blood coagulation data by the thrombelastography device body, the second inclination state and the vibration state of the thrombelastography device body may be acquired. The blood coagulation data measured by the thrombelastography device body is corrected according to the second inclination state and the vibration state, thereby eliminating or reducing the error caused by the inclination or vibration of the thrombelastography device body, and improving the accuracy of measuring the blood coagulation data of blood.

11. In the embodiment of the present invention, the rotary shaft rotates relative to the fixed support part under the driving force of the measured blood and drives the movable support part to rotate. The movable support part drives the magnet to move to cause a change in the magnetic field of the magnet. The Hall element outputs the measurement electric signal according to the magnetic field change of the magnet. The processing unit determines the blood coagulation data of the measured data according to the measurement electric signal. The magnetic shielding unit shields the influences of the external magnetic field on the Hall element and the magnet, such that the magnetic field change of the magnet, which are measured by the Hall element, more accurately reflects the blood coagulation data, the processing unit obtains more accurate blood coagulation data, and the measurement accuracy of the measured blood is improved.

12. In this embodiment, since the Hall element extends into the magnetic shielding unit by means of the first connection rod, the magnetic shielding unit has a better effect of protecting the Hall element away from the influences from the external magnetic field. In addition, the Hall element is fixedly connected to the fixed support part by means of the first connection rod. Since the Hall element is stationary, when the magnet moves along with the movable support part, the Hall element may more accurately measure the magnetic field change of the magnet.

13. In this embodiment, since the magnet extends into the magnetic shielding unit by means of the second connection rod, the magnetic shielding unit has a better effect of protecting the magnet away from the influences from the external magnetic field, such that the Hall element can more accurately measure the magnetic field change of the magnet.

14. In the embodiment of the present invention, the rotary shaft rotates relative to the fixed support part under the driving force of the measured blood and drives the movable support part to rotate. The movable support part rotates with the connection part as an axis. In the connection part, since the contact area between the top cone and the jewel bearing is relatively small, the frictional force between the top cone and the jewel bearing is relatively small. When the movable support part rotates with the rotary shaft, the frictional force has less resistance to the rotation, thereby reducing the influence of the frictional force on the magnetic field change of the magnet, so that the magnetic field change of the magnet more accurately reflects the blood coagulation data of the measured blood.

15. In the embodiment of the present invention, the box body is made of a ferromagnetic material. The magnetic permeability of the ferromagnetic material is several thousand times greater than the magnetic permeability of air, but the magnetic reluctance of a cavity is much larger than that of the ferromagnetic material. The vast majority of magnetic lines of the external magnetic field will pass through the walls of the box body, but a small amount of magnetic fluxes enter into the box body. In this way, there is substantially no external magnetic field in the cavity inside the box body, so as to shield the external magnetic field. After the external magnetic field is shielded by the box body, the magnetic field change measured by the Hall element is not disturbed by the external magnetic field, so that the measurement result is more accurate, and the blood coagulation data determined by the processing unit is more accurate.

It can be appreciated that, while the terms "first", "second" and so on may be used herein to distinguish one entity or operation from another, it does not require or imply such a relation or sequence between these entities or operations. Further, the terms "include", "comprise" or any variation thereof are intended to cover an nonexclusive containing, such that a process, a method, an item or a device containing a series of elements not only includes these elements, but also includes other elements that are not set forth specifically, or also includes an inherent element of such a process, method, item or device. Without further limitation, an element defined by a phrase "include a" does not mean that other elements are excluded from the process, method, item or device.

Aspects

The various aspects numbered below further provide the disclosure of the present invention. It should be noted that any of the following aspects 1-11 may be combined with any of the aspects 12-14, may also be combined with any aspect 15-20, may also be combined with any aspect 21-23, may also be combined with any aspect 24-25, and may also be combined with aspect 26. In addition, any of the following aspects 12-14 may be combined with any of the aspects 15-20, may also be combined with any of the aspects 21-23, may also be combined with any of the aspects 24-25, and may also be combined with aspect 26. Any of the following aspects 15-20 may be combined with any aspect 21-23, may also be combined with any aspect 24-25, and may also be combined with aspect 26. Any of the following aspects 21-23 may be combined with any aspect 24-25 and may also be combined with aspect 26. Any of the following aspects 24-25 may be combined with aspect 26.

1. An apparatus for measuring blood coagulation data, comprising a movable support part, a fixed support part, a connection part, a rotary shaft, a magnet, a Hall element, and a processing unit; wherein one end of the movable support part is fixedly connected to the rotary shaft, and the other end of the movable support part is connected to the fixed support part by means of the connection part;

the movable support part is fixedly connected to the magnet;

the rotary shaft is able to rotate relative to the fixed support part under the driving force of measured blood and drive the movable support part to rotate;

the movable support part is able to move the magnet to cause a change in the magnetic field of the magnet;

the Hall element is connected to the processing unit;

the Hall element is used for outputting a measurement electric signal according to the magnetic field change of the magnet; and the processing unit is used for determining blood coagulation data of the measured blood according to the measurement electric signal.

2. The apparatus according to aspect 1, wherein a Hall element comprises a Hall sheet;

an N pole and an S pole of the magnet are located on the same plane; and an included angle between a sensing surface where the Hall sheet is located and the surface where the N pole and the S pole of the magnet are located is (0°, 90°].

3. The apparatus according to aspect 1, wherein the connection part comprises a top cone and a jewel bearing;

the jewel bearing is fixed on the fixed support part;

the top cone is fixed on the movable support part; and the top cone and the jewel bearing are connected in a point contact manner, wherein a contact area of the point contact is less than a preset area.

4. The apparatus according to aspect 1, wherein the connection part comprises a first magnet and a second magnet;

the first magnet is fixed on the fixed support part;
the second magnet is fixed on the movable support part; and
magnetic suspension is formed between the first magnet and the second magnet, such that the fixed support part and the movable support part are connected by means of the magnetic suspension.

5. The apparatus according to aspect 1, further comprising:
at least one hair spring;
an inner ring of the hair spring is fixedly connected to an outer circumferential surface of the rotary shaft;
an outer ring of the hair spring is fixedly connected to the fixed support part; and
the hair spring is configured to, after the rotary shaft rotates away from a balanced position of the rotary shaft, produce an acting force which rotates the rotary shaft towards the balanced position.

6. The apparatus according to any one of aspects 1 to 5, wherein
the Hall element is fixedly connected to the fixed support part;
and/or
the N pole and the S pole of the magnet are located on the same plane.

7. The apparatus according to aspect 1, further comprising a magnetic shielding unit which is configured to shield the influences of an external magnetic field on the Hall element and the magnet.

8. The apparatus according to aspect 7, further comprising a first connection rod, wherein
the magnetic shielding unit is provided with a first via hole; and
one end of the first connection rod is fixedly connected to the fixed support part, and the other end of the first connection rod passes through the first via hole in the magnetic shielding unit, extends into the magnetic shielding unit and is fixedly connected to the Hall element.

9. The apparatus according to aspect 7, further comprising a second connection rod, wherein
the magnetic shielding unit is provided with a second via hole; and
one end of the second connection rod is fixedly connected to the movable support part, and the other end of the second connection rod passes through the second via hole in the magnetic shielding unit, extends into the magnetic shielding unit and is fixedly connected to the magnet.

10. The apparatus according to any one of aspects 7 to 9, wherein
the magnetic shielding unit comprises a magnetic shielding mesh cover made of a ferromagnetic material, or a box body made of a ferromagnetic material;
or
the magnetic shielding unit comprises a support cylinder and a shielding layer; wherein the shielding layer is formed by winding the support cylinder with a metal conductive shielding tape.

11. The apparatus according to any one of aspects 7 to 9, wherein
the processing unit is configured to determine a rotation angle of the rotary shaft according to an amplitude of the measurement electric signal and a formula I, and determine blood coagulation data of the measured blood according to the rotation angle;
the formula I includes:

$$W = D \times I,$$

wherein W is the rotation angle, I is the amplitude of the measurement electric signal, and D is a proportional coefficient of the amplitude of the measurement electric signal and the rotation angle.

12. A use method for measuring blood coagulation data according to any one of aspects 1 to 11, comprising the following steps:
placing the rotary shaft in measured blood;
driving the rotary shaft by the measured blood, such that the rotary shaft rotates relative to the fixed support part;
driving, by the rotary shaft, the movable support part to rotate;
driving, by the movable support part, the magnet to move;
outputting, by the Hall element, a measurement electric signal according to a change in the magnetic field of the magnet; and
determining, by the processing unit, the blood coagulation data of the measured blood according to the measurement electric signal.

13. The method according to aspect 12, wherein
the operation of driving, by the movable support part, the magnet to move includes:
driving, by the movable support part, the magnet to move, such that the magnet rotates within a plane where the N pole and the S pole of the magnet are located.

14. The method according to aspect 12, wherein
after the movable support part drives the magnet to move and before the Hall element outputs the measurement electric signal according to the change in the magnetic field of the magnet, the method further comprises:
shielding, by the magnetic shielding element, the influences of an external magnetic field on the Hall element and the magnet.

15. A apparatus for measuring blood coagulation data, comprising a thrombelastography device body, a position measurement module, a control module and a horizontal calibration module; wherein
the position measurement module is configured to measure a first inclination state of the thrombelastography device body, and send information on the first inclination state to the control module;
the control module is configured to determine whether the thrombelastography device body is in a horizontal position according to the first inclination state, form a corresponding control instruction according to the first inclination state if the thrombelastography device body is not in the horizontal position, and send the control instruction to the horizontal calibration module; and
the horizontal calibration module is configured to perform horizontal calibration processing on the thrombelastography device body according to the control instruction.

16. The apparatus according to aspect 15, wherein
the horizontal calibration module comprises at least one lifting unit;
one end of each lifting unit is fixed on the edge of a base of the thrombelastography device body, and the other end of the thrombelastography device body is in contact with a support platform for supporting the thrombelastography device body; and
the lifting unit is configured to be extended or shortened according to the control instruction, such that the edge of the base ascends or descends.

17. The apparatus according to aspect 16, further comprising two fixed fulcrums in the case of one lifting unit, wherein one end of each of the two fixed fulcrums is fixed to the edge of the base of the thrombelastography device body, and the other end of the fixed fulcrum is in contact with the support platform; and the two fixed fulcrums and the lifting unit are arranged in a triangle on the base of the thrombelastography device body.

18. The apparatus according to aspect 16, wherein the lifting unit comprises a motor, a screw rod and a nut;

the nut is fixed to the edge of the base of the thrombelastography device body and is meshed with the screw rod;

one end of the screw rod is fixedly connected to an output shaft of the motor, and the other end of the screw rod is in contact with the support platform;

the motor rotates forwardly or reversely according to the control instruction to change the relative positions of the nut and the screw rod, such that the edge of the base ascend or descends.

19. The apparatus according to aspect 16, wherein the lifting unit comprises a hydraulic support rod and a hydraulic pump;

one end of the hydraulic support rod is fixed to the edge of the base of the thrombelastography device body, and the other end of the hydraulic support rod is in contact with the support platform;

the hydraulic pump is connected to the hydraulic support rod and configured to supply power to the hydraulic support rod according to the control instruction, such that the hydraulic support rod is extended or shortened to cause the edge of the base to ascend or descend.

20. The apparatus according to any one of aspects 15 to 19, further comprising a vibration measurement module and a data correction module; wherein the position measurement module is further configured to measure a second inclination state of the thrombelastography device body in a process of measuring the blood coagulation of blood, and send the second inclination state to the data correction module;

the vibration measurement module is configured to measure a vibration state of the thrombelastography device body in the process of measuring the blood coagulation of the blood, and send the vibration state to the data correction module; and the data correction module is configured to correct the blood coagulation data measured by the thrombelastography device body according to the second inclination state and the vibration state.

21. A calibration method for the apparatus for measuring blood coagulation data according to aspects 15 to 20, comprising the following steps:

measuring a first inclination state of the thrombelastography device body in the apparatus for measuring blood coagulation data;

determining whether the thrombelastography device body is in a horizontal position according to the first inclination state;

forming a corresponding control instruction according to the first inclination state if the thrombelastography device body is not in the horizontal position; and performing horizontal calibration processing on the thrombelastography device body according to the control instruction.

22. The calibration method according to aspect 21, wherein the operation of performing horizontal calibration processing on the thrombelastography device body includes:

causing the edge of the base of the thrombelastography device body to ascend or descend according to the control instruction to adjust an included angle between the base and the horizontal plane, and adjusting the thrombelastography device body to the horizontal position.

23. The calibration method according to aspect 21 or 22, further comprising: measuring a second inclination state of the thrombelastography device body in the process of measuring the blood coagulation of blood;

measuring a vibration state of the thrombelastography device body in the process of measuring the blood coagulation of blood; and correcting the blood coagulation data measured by the thrombelastography device body according to the second inclination state and the vibration state.

The present invention may be implemented in other forms without departing from the spirit and novel characteristics of the present invention. Various embodiments disclosed in the present application should be considered in all aspects in an illustrative manner, rather than a restrictive manner. The scope of the present invention is claimed by the appended aspects rather than by the foregoing description; all modifications made within the equivalent meanings and equivalent scope of the various aspects are intended to be included within the protection scope of the present invention.

24. A bracket, comprising a fixed support part, a movable support part and a connection part; wherein the connection part comprises a first fixing connection member and a second fixing connection member;

the first fixing connection member is fixedly connected to the fixed support part;

the second fixing connection member is fixedly connected to the movable support part;

the first fixing connection member and the second fixing connection member are connected together in a manner of point connection;

the movable support part is fixedly connected to an external supported object; and the movable support part is driven by the supported object to rotate relative to the fixed support part by means of the point connection between the first fixing connection member and the second fixing connection member.

25. The bracket according to aspect 24, wherein the first fixing connection member comprises a jewel bearing, and the second fixing connection member comprises a top cone;

or the first fixing connection member comprises a top cone, and the second fixing connection member comprises a jewel bearing; wherein the jewel bearing may be of a cake structure; a plane of the cake structure is provided with a tapered groove; the top cone may be of a tapered structure; the tip of the top cone is located in the tapered groove on the jewel bearing; and the top cone is connected to the jewel bearing in a manner of point contact.

26. A thrombelastography device body, comprising a rotary shaft and the bracket according to any of aspects 24 to 25, wherein the rotary shaft which serves as the supported object is fixedly connected to the movable support part in the bracket; and the rotary shaft drives the movable support part to rotate under the driving force of the measured blood.

The present invention may be implemented in other forms without departing from the spirit and novel characteristics of the present invention. Various embodiments disclosed in the present application should be considered in all aspects in an illustrative manner, rather than a restrictive manner. The scope of the present invention is claimed by the appended aspects rather than by the foregoing description; all modifications made within equivalent meanings and equivalent scope of the various aspects are intended to be included within the protection scope of the present invention.

The invention claimed is:

1. An apparatus for measuring blood coagulation data, comprising:
   a movable support part;
   a fixed support part;
   a connection part;
   a rotary shaft;
   a magnet;
   a Hall element; and
   a processing unit,
   wherein
   one end of the movable support part is fixedly connected to the rotary shaft, and the other end of the movable support part is connected to the fixed support part by means of the connection part,
   the movable support part is fixedly connected to the magnet,
   the connection part comprises at least one of:
      a top cone and a jewel bearing, the jewel bearing fixed on the fixed support part, the top cone fixed on the movable support part, the top cone and the jewel bearing connected in a point contact manner, and a contact area of the point contact being less than a preset area, and
      a first magnet and a second magnet, the first magnet fixed on the fixed support part, the second magnet is fixed on the movable support part, and magnetic suspension is formed between the first magnet and the second magnet, such that the fixed support part and the movable support part are connected by means of the magnetic suspension;
   the rotary shaft is able to rotate relative to the fixed support part under the driving force of measured blood and drive the movable support part to rotate,
   the movable support part is able to move the magnet to cause a change in the magnetic field of the magnet
   the Hall element is connected to the processing unit,
   the Hall element is used for outputting a measurement electric signal according to the magnetic field change of the magnet, and
   the processing unit is used for determining blood coagulation data of the measured blood according to the measurement electric signal.

2. The apparatus according to claim 1, wherein
   the Hall element comprises a Hall sheet,
   an N pole and an S pole of the magnet are located on the same plane, and
   an included angle between a sensing surface where the Hall sheet is located and the plane where the N pole and the S pole of the magnet are located is 0 degrees or 90 degrees.

3. The apparatus according to claim 1, wherein the connection part comprises the top cone and the jewel bearing.

4. The apparatus according to claim 1, wherein the connection part comprises the first magnet and the second magnet.

5. The apparatus according to claim 1, further comprising:
   at least one hair spring, wherein
   an inner ring of the hair spring is fixedly connected to an outer circumferential surface of the rotary shaft,
   an outer ring of the hair spring is fixedly connected to the fixed support part, and
   the hair spring is configured to: after the rotary shaft rotates away from a balanced position of the rotary shaft; produce an acting force which rotates the rotary shaft towards the balanced position.

6. The apparatus according to claim 1, wherein the Hall element is fixedly connected to the fixed support part.

7. The apparatus according to claim 1, further comprising:
   a magnetic shielding unit configured to shield the influences of an external magnetic field on the Hall element and the magnet.

8. The apparatus according to claim 7, wherein
   the processing unit is configured to determine a rotation angle of the rotary shaft according to an amplitude of the measurement electric signal and a formula Y, and determine blood coagulation data of the measured blood according to the rotation angle,
   the formula Y includes:

$$W = D \times I,$$

in which W is the rotation angle, I is the amplitude of the measurement electric signal, and D is a proportional coefficient of the amplitude of the measurement electric signal and the rotation angle.

9. A use method for measuring blood coagulation data according to claim 1, comprising:
   placing the rotary shaft in measured blood;
   driving the rotary shaft by the measured blood, such that the rotary shaft rotates relative to the fixed support part;
   driving, by the rotary shaft, the movable support part to rotate;
   driving, by the movable support part, the magnet to move;
   outputting, by the Hall element, a measurement electric signal according to a change in the magnetic field of the magnet; and
   determining, by the processing unit, the blood coagulation data of the measured blood according to the measurement electric signal.

10. The method according to claim 9, wherein
    after the movable support part drives the magnet to move and before the Hall element outputs the measurement electric signal according to the change in the magnetic field of the magnet, the method further comprises:
    shielding, by the magnetic shielding element, the influences of an external magnetic field on the Hall element and the magnet.

11. An apparatus for measuring blood coagulation data, comprising: a thrombelastography device body; a position measurement module; a control module; and a horizontal calibration module, wherein
    the position measurement module is configured to measure a first inclination state of the thrombelastography device body, and send information on the first inclination state to the control module,
    the control module is configured to determine whether the thrombelastography device body is in a horizontal position according to the first inclination state, form a corresponding control instruction according to the first inclination state if the thrombelastography device body is not in the horizontal position, and send the control instruction to the horizontal calibration module, and
    the horizontal calibration module is configured to perform horizontal calibration processing on the thrombelastography device body according to the control instruction.

12. The apparatus according to claim 11, further comprising:
- a vibration measurement module; and
- a data correction module, wherein
- the position measurement module is further configured to measure a second inclination state of the thrombelastography device body in a process of measuring the blood coagulation of blood, and send the second inclination state to the data correction module,
- the vibration measurement module is configured to measure a vibration state of the thrombelastography device body in the process of measuring the blood coagulation of blood; and send the vibration state to the data correction module, and
- the data correction module is configured to correct the blood coagulation data measured by the thrombelastography device body according to the second inclination state and the vibration state.

13. A calibration method for the apparatus for measuring blood coagulation data according to claim 11, comprising:
- measuring a first inclination state of the thrombelastography device body in the apparatus for measuring blood coagulation data;
- determining whether the thrombelastography device body is in a horizontal position according to the first inclination state;
- forming a corresponding control instruction according to the first inclination state if the thrombelastography device body is not in the horizontal position; and
- performing horizontal calibration processing on the thrombelastography device body according to the control instruction.

14. A bracket, comprising: a fixed support part; a movable support part; and a connection part, wherein
- the connection part comprises a first fixing connection member and a second fixing connection member, wherein
  - the first fixing connection part comprises a jewel bearing, and the second fixing connection part comprising a top cone, or
  - the first fixing connection part comprises a top cone, and the second fixing connection part comprises a jewel bearing,
- the first fixing connection member is fixedly connected to the fixed support part,
- the second fixing connection member is fixedly connected to the movable support part,
- the first fixing connection member and the second fixing connection member are connected together in a manner of point connection,
- the movable support part is fixedly connected to an external supported object, and
- the movable support part is driven by the supported object to rotate relative to the fixed support part by means of the point connection between the first fixing connection member and the second fixing connection member.

15. An apparatus for measuring blood coagulation data, comprising: the supported object which is a rotary shaft and the bracket of claim 14; wherein
- the rotary shaft is fixedly connected to the movable support part in the bracket, and
- the rotary shaft drives the movable support part to rotate under the driving force of the measured blood.

* * * * *